United States Patent [19]
Lichti et al.

[11] Patent Number: 5,403,813
[45] Date of Patent: Apr. 4, 1995

[54] CONTROLLED RELEASE COMPOSITION OF BIOCIDE IN AN AQUEOUS DISPERSION OF VISCOUS OIL

[75] Inventors: Gottfried Lichti, Essendon; Anthony G. Flynn, Horsham; Alexander Serban, Doncaster; Darren J. Park, Dandenong; William R. Jackson, Glen Waverley; Janine J. Kibblewhite, Balaclava; Paul A. Horne, Warrandyte; Daryl K. Wood, Greensborough, all of Australia; Jin L. Chen, Richmond, Calif.

[73] Assignee: Daratech Proprietary Limited, Melbourne, Australia

[21] Appl. No.: 946,442

[22] PCT Filed: May 17, 1991

[86] PCT No.: PCT/AU91/00218
§ 371 Date: Jan. 18, 1993
§ 102(e) Date: Jan. 18, 1993

[87] PCT Pub. No.: WO91/17657
PCT Pub. Date: Nov. 28, 1991

[30] Foreign Application Priority Data
May 18, 1990 [AU] Australia .................. 0209/90

[51] Int. Cl.$^6$ ............ A01N 25/04; A01N 33/18; A01N 37/22; A01N 57/16
[52] U.S. Cl. .................. 504/116; 504/342; 504/347; 71/DIG. 1; 514/89; 514/789; 514/938; 424/405
[58] Field of Search .............. 504/116, 347, 342; 71/DIG. 1; 514/89, 787; 424/405

[56] References Cited

U.S. PATENT DOCUMENTS

| | | | |
|---|---|---|---|
| 1,363,207 | 1/1972 | Bouvet et al. | 424/219 |
| 4,334,910 | 6/1982 | Lörincz et al. | 71/DIG. 1 |
| 4,695,312 | 9/1987 | Hayase et al. | 504/281 |
| 5,137,563 | 8/1992 | Valkanas | 71/64.07 |

FOREIGN PATENT DOCUMENTS

| | | |
|---|---|---|
| 46840335 | 1/1970 | Australia . |
| 35914380 | 12/1980 | Australia . |
| 20021477 | 1/1981 | European Pat. Off. . |

OTHER PUBLICATIONS

Patent Abstract of JP 52007437, Solvent for e.g. herbicides, insecticides and fungicides–comprises hydrocarbon mixt. contg. aromatic component liq. at room temp. (20 Jan. 1977).

Patent Abstract of JP 58172304, Ant controlling agent obtd. by dispersing or dissolving active cpd. in machine oil and adding anionic and nonionic surfactants (10 Nov. 1983).

S. A. De Licastro et al. "The relation between viscosity and penetration of some diethyl p-substituted phenyl phosphorothionates and oil carries into the cuticle of *Triatoma infestans*" Pesticide Biochemistry and Physiology 19:53–59 (1983).

*Primary Examiner*—Peter O'Sullivan
*Assistant Examiner*—S. Mark Clardy
*Attorney, Agent, or Firm*—Walter H. Dreger; Jan P. Brunelle

[57] ABSTRACT

A controlled release agricultural composition comprising an aqueous dispersion of: 1) a water insoluble matrix comprising a viscous oil (i.e., a hydrocarbon crude oil or post-refining residual oil) selected from the group consisting of bitumen, abietic acid, ester derivatives of abietic acid, carboxylic acid containing materials, and carboxylic acid ester containing materials, and 2) at least one active ingredient, which has a melting point of less than 140° C. and is soluble in the viscous oil matrix, selected from the group consisting of herbicides, insecticides, fungicides, and nematicides.

14 Claims, 19 Drawing Sheets

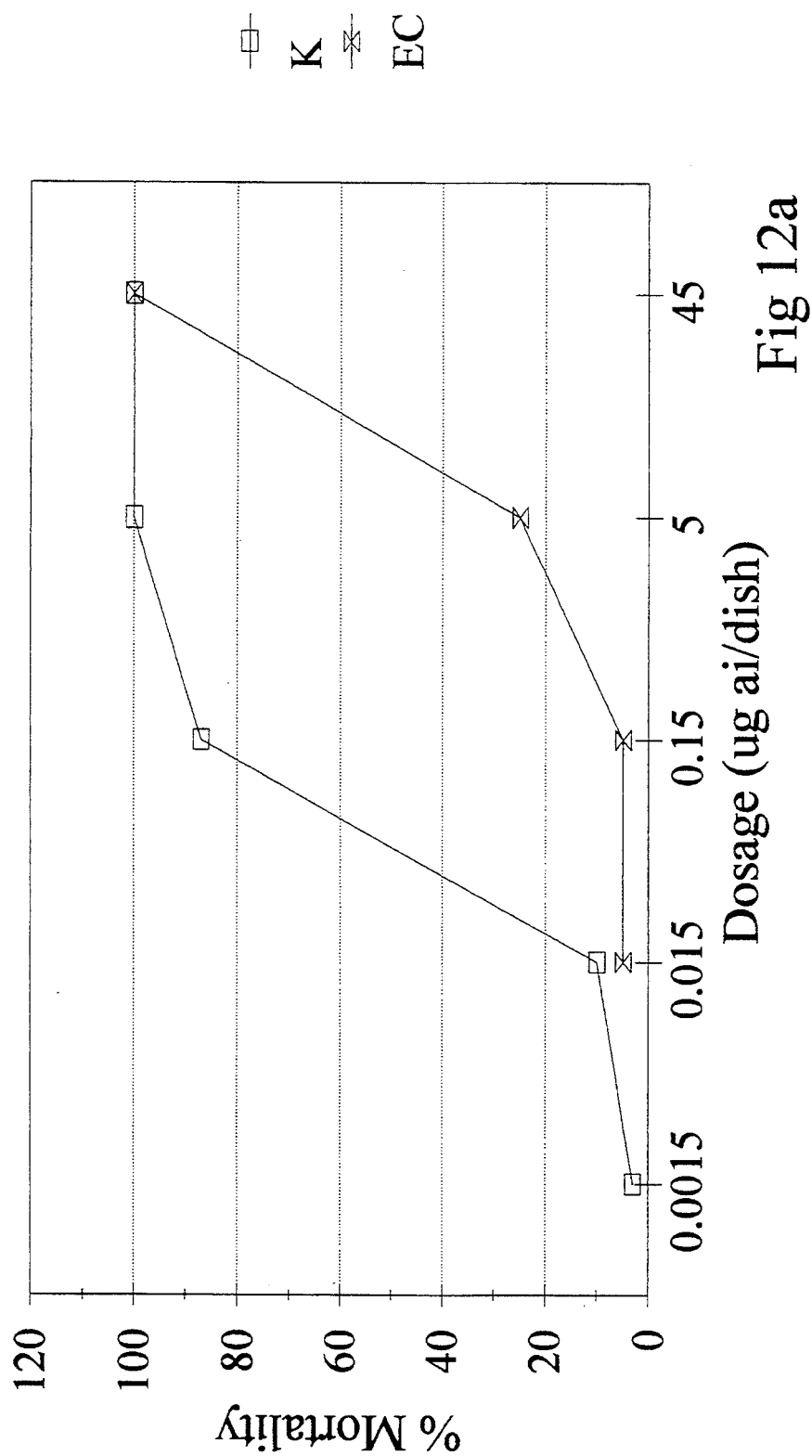

CONTROLLED RELEASE COMPOSITION OF BIOCIDE IN AN AQUEOUS DISPERSION OF VISCOUS OIL

FIELD OF THE INVENTION

This invention relates to improved controlled release compositions that allow an active ingredient to be released in a controlled manner, and in particular to such compositions that are in the form of aqueous dispersions. The invention also relates to methods of preparing controlled release compositions in the form of an aqueous dispersion.

1. Background of the Invention

Controlled release formulations in the form of aqueous emulsions have been previously disclosed in PCT/AU 89/00230.

There are several ways in which the use of such types of controlled release formulations in the form of aqueous dispersions can be of increased benefit relative to known compositions of active.

1. The controlled release formulation may decrease the rate of release of active ingredient from the formulation, leading to a longer period of efficacy or, if the active is volatile, leading to reduced loss of active to the atmosphere.
2. The controlled release formulation may be safer to handle and store.
3. The controlled release formulation may contain less volatile solvent.
4. The controlled release formulation may be less harmful to beneficial species. For example, a controlled release cereal herbicide may be less damaging to germinating wheat than a standard formulation such as an emulsion concentrate.
5. The controlled release formulation may enhance the potency of the active ingredient, for example by improving the uniformity of distribution of the active ingredient in soil.

2. Summary of Prior Art

Previous aqueous dispersions for the controlled release of active ingredients have included the following types:

a. Dispersions where a chemical reaction occurs after the formation of the dispersion, creating a solid matrix from an originally liquid disperse phase. Examples include the formulation of poly-urea capsules and the formation of a polymer matrix from liquid monomers by polymerisation. Specific examples are disclosed in Australian Patent Application No. 37393/85 and U.S. Pat. No. 3,212,967.

b. Dispersions where an organic solvent is removed from the disperse phase after the formation of the dispersion, leaving a solid disperse mass as host matrix, for example the formation of polylactide micro-capsules. An example is disclosed in Japanese Patent Application No. 48923/85.

c. Dispersions in which a solid coating is formed on the outer boundary of the disperse phase by the process of polymer coacervation (i.e. controlled precipitation of polymers at the interface). An example is disclosed in British Patent No. 929405.

d. Dispersions in which the matrix is heated to elevated temperatures prior to the addition of the active ingredient or ingredients, and in which the molten mass is added with vigorous stirring to an aqueous phase in the presence of surfactants to form a stable emulsion.

This last type of dispersion has been alleged to be useful in the following cases:

(i) Composition for the protection of wood using a dispersion of fungicide and insecticide in an oily matrix (Pojurowski French Patent Publication No. 2,392,787).

(ii) Composition with improved biocidal properties using a dispersion e.g. of pentachlorophenol in paraffin (Mobil Australian Patent Application No. 19222/70). In this instance, it was observed that the dispersions were also useful for imparting water resistant properties to treated surfaces (e.g. wood).

Using these compositions, the delivery of active ingredient at the site of application of the composition may occur at a reduced rate when compared with the performance of standard compositions of the same active substance.

In many cases it is important to decrease the rate of release of active ingredient from the controlled release formulation relative to the rate of release of active from the standard formulation by a considerable amount before significant product advantages can be obtained. This advantage is usually sought in terms of increased efficacy of the controlled release formulation. See for example, the publication of Marvin M. Schreiber et al in "Weed Science" Vol 35 No. 3 pages 407–11 (1987).

The required reduction of release rate in the controlled release product depends on both the nature of the active ingredient and on the performance of the standard formulation of the active material.

It is an object of the present invention to provide improved controlled release compositions and in particular controlled release formulations of dinitroaniline herbicides, chloroacetanilide herbicides and organophosphate insecticides, preferably trifluralin, metolachlor and chlorpyrifos where the formulations show decreased volatile loss of active ingredient and/or reduced phytotoxicity to crops in field applicants and/or increased or equal efficacy.

The invention also relates to methods of preparing controlled release compositions in the form of aqueous dispersions.

The term "viscous oil" is defined for the purposes of this invention as any naturally occurring hydrocarbon crude oil or any residual oil remaining after refining operations which is generally characterised by a viscosity of about $10^2$–$10^6$ centipoise or greater and otherwise generally, but not necessarily, characterised by an API gravity of about 20° API or less, high metal content, high sulfur content, high asphaltene content and/or high pour point. The term "viscous oil" it is to be understood also to encompass the following: vacuum residuals, vis-breaker residuals, catalytic-cracker residuals, catalytic hydrogenated residuals, coker residuals, ROSE (residual oil supercritical extraction) residuals, tars and cut-back tars, bitumen, pitch and any other terms describing residuals of hydrocarbon processing. The term "viscous oil" encompasses naturally occurring viscous crude oils (also called heavy crude oils) as well as residual bottom-of-the-barrel products from refineries, such as vacuum residues and other residual fuel oils and asphalt. While low gravity does not necessarily coincide with high density, these characteristics are generally correlated in viscous hydrocarbons.

Generally the following characteristics are considered typical of the types of crude oils and residual oils which are useful for the present invention.

1. Low API gravity, generally at or below 20° API. This is the most frequently use criterion, both because it is easily measured and because 20° API crude roughly corresponds to the lower limit recoverable with conventional production techniques.
2. Viscosities in the range of about $10^2$ to $10^6$ centipoise (cp) or even higher in some cases. For those materials that are solids at ambient temperatures it is a requirement that they have a viscosity of at least 100 centipoise at 120° C.
3. High metal contents. For example, heavy crudes often have nickel and vanadium contents as high as 500 ppm.
4. High sulfur content, eg, 3 weight percent or more.
5. High asphaltene content.
6. High pour point.

The "viscous oils" can be generally defined as having a paraffin content of about 50% by weight or less and an aromatic content of about 15% by weight or greater with viscosities of about 100 centipoise or greater at 65°. The viscous residuals generally are characterised by a paraffin content in the range from about 4% to about 40% by weight, an aromatic content in the range from about 15% to about 70% by weight and an asphaltene content from about 5% to about 80% by weight.

In addition, the term "viscous oil" includes heads and bottoms of crude tall oil (a wood derivative) abietic acid, especially as wood rosin and chemical derivatives of abietic acid eg, the maleic anhydride adduct of abietic acid and especially chemical derivatives of abietic acid which exhibit ester functionality, eg the condensation product of abietic acid, maleic anhydride and glycerol. Other polyhydric alcohols may also be used, though glycerol is preferred. Other viscous hydrocarbons suitable for this invention are the bottoms of any distillation column of processes used to extract natural oils eg, eucalyptus oil.

In addition, the term "viscous oil" includes substances which are solid at room temperature but become viscous oils as described herein in the range 20°–120° C.

Preferably the "viscous oil" is selected from heads and bottoms of crude tall oil, distillation bottoms of oil extraction processes (oil of mineral natural vegetable or animal origin), wood rosin, and derivatives of wood rosin. More preferably the "viscous oil" is selected from bitumen, wood rosin, derivatives of wood rosin with ester functionality and mixtures of above. The "viscous oil" may also be selected from materials having carboxylic acid groups or carboxylic acid ester groups such as maleic ester residues.

Stabilising amounts of surfactants are present in compositions of our invention. Combinations of surfactant types such as non-ionic and anionic are particularly useful. Preferred ionic surfactants are: calcium dodecyl benzene sulphonate (linear or branched chain), metal and amine salts of organic acids (eg, stearic, oleic and abietic acid) amine ethoxylates and primary, secondary and tertiary alkylamines.

Preferred non-ionic surfactants are amine ethoxylates and alkylphenol ethoxylates and ethoxylates and propoxylates of polyhydric alcohols such as sorbitol and glycerol. Other preferred suffactants are copolymers of polyoxyethylene and polyoxypropylene, and alkyl and alkylphenol adducts of such copolymers.

Further preferred surfactants are Vinsol (trademark of Hercules Pry Ltd), alpha oleum sulphonate, alkyl dimethyl benzyl ammonium chloride and cetyl trimethyl ammonium bromide.

Preferably a mixture of ionic and non-ionic surfactants are used and especially preferred are combinations of anionic and non-ionic surfactants.

Any of the surfactants of the formulation may be added to the oil phase or the aqueous phase, or to both.

In choosing the appropriate surfactants for the invention, the physical stability of the emulsion was an important criteria. Stability ensures that there is adequate shelf stability for a commercial product.

Stability of emulsions was assessed using the following criteria:

i) Particle Size

Emulsions were diluted, 1% in water and viewed under a microscope. A subjective determination of common particle size range was performed and degree of flocculation was also noted.

ii) Dispersability in Water

Emulsions were diluted 1% in water and ease of dispersion was assessed by eye.

iii) Appearance and Colour

The colour and appearance of the emulsion was observed immediately after preparation. The colour was used as an initial estimation of particle size. For coloured matrices, a paler appearance was taken to indicate smaller particle size.

iv) Bench Stability

Inversion: The resistance of emulsions was measured to ensure emulsions were water external. This was performed with a multimeter using standard procedure.

Phasing: Any gross settling of particles was deemed unacceptable as determined by the eye.

Crystallisation: The surface and bulk of emulsions were inspected regularly by eye to note the first signs of crystallization and hence failure to yield a stable emulsion. Results were confirmed by examination of emulsions under an optical microscope using crossed polarising lenses.

The following studies used trifluralin as the active material and bitumen as the matrix material. A range of nonionic surfactants including: nonyl phenol ethoxylates, other fatty alcohol ethoxylates, and fatty amine ethoxylates was evaluated in combination with an anionic emulsifier. The ratio of anionic emulsifier (e.g. vinsol resin) and nonionic emulsifier and the HLB of the various nonionic surfactants were investigated over a number of differing ratios. Emulsions were prepared using these surfactant systems and were assessed according to the criteria listed above (see Table I). All of the emulsions based on the vinsol resins displayed totally unacceptable stability, (that is the emulsions inverted, produced massive crystallization or gross synerysis on storage at ambient temperatures over periods of time from 1 hour to 2 weeks.

Due to the unacceptable performance of the vinsol resin anionic surfactants different types of anionic emulsifiers were investigated. Fatty acids neutralised with amine or metal salts in combination with fatty amine ethoxylates were found to yield emulsions with improved stability. Different fatty acids, including oleic acid, linoleic acid, lauric acid, stearic were assessed in combination with fatty amine ethoxylates of various HLB values. Emulsions were prepared using combinations of fatty acids and amine ethoxylates and the surfactants were optimised to yield the best emulsion stability.

Concomitantly fatty quaternary ammonium surfactants in combination with fatty alcohol ethoxylates were also found to yield emulsions with improved stability. However, the viscosity of these emulsions was too high and led to poor dispersability in water.

Another class of surfactants investigated was calcium dodecyl benzene sulphonate in combination with alkyl and alkylaryl polyoxyalkylene oxide ether condensates. These suffactants were found to yield emulsions with particle sizes typically less than 2 um treat displayed excellent disperability and suspendability when diluted in water and good shelf stability. Again, the ratio of anionic to nonionic emulsifier was adjusted to optimise emulsion stability. (see Table I).

The resulting emulsion using bitumen as the controlled release matrix had a viscosity of 1500 cp. The droplet size of the emulsion was typically less than 2 um. After two months storage at ambient temperature there was no sign of trifluralin crystallization, droplet coalescene or emulsion deterioration as determined by techniques well known in the art.

For bitumen matrix at high oil ratios we departed from the conventional an by dissolving all nonionic and ionic emulsifier components in the aqueous phase. This preferred method was found to yield emulsions of superior stability with smaller particle size, less prone to crystallization. It is thought that dissolving the suffactants in the aqueous phase enables rapid migration of suffactants to the interface and hence minimization of particle size.

The conventional art as applied to bitumen containing emulsions discloses the use of certain anionic suffactants (eg vinsol mixed with oleic and neutralised to pH 12) or blends of anionic and nonionic surfactants (eg ameroxyl OE10 (high HLB), plus vinsol neutralised to pH 12 in the aqueous phase, and Ameroxyl OE2 (low HLB) in the non-aqueous phase. The purpose of neutralising vinsol to PHI2 was to promote the anionic character of the emulsifier. The role of the nonionic surfactant was to achieve a degree of steric stabilisation. This was not achieved to an adequate extent because the conventional systems were shown to be unstable (Table 1).

The stability of surfactant systems was investigated by looking at classes of surfactants which were anticipated to promote a sufficient degree of steric stabilisation and charge stabilisation in the dispersed phase and promote fine droplet size. Surfactants were selected on the basis of the following characteristics:

Ionic suffactants displaying low water solubility, molecular weight in the range of from 100–400 a.m.u. It was thought that suffactants displaying the above characteristics would provide a uniform charge distribution over the dispersed particle droplets and promote good interfacial packing with elected non-ionic emulsifiers.

Non-ionic suffactants with relatively high molecular weight (1500–4000), high HLB (12–17), and potential multiple anchoring sites to promote strong adhesion to the dispersed particle surface. For example alkyl phenol propoxylates/ethoxylates are suitable.

Blends of anionic and non-ionic suffactants displaying the above characteristics were mixed to optimum ratios. Optimum ratios were determined by screening the different blends of anionic and non-ionic suffactants using criteria (i-iv) as described above. Ratios of between 80:20 to 20:80 anionic:nonionic were found to work. For example using bitumen/trifluralin preferably surfactant ratios of from 60:40 to 40:60 were utilised (see Examples 4 and 5). The most preferred anionic:nonionic surfactant ratio was 50:50 (Example 6).

It is believed that the above ratios worked because the propylene oxide block in the nonionic surfactant provides multiple anchoring sites on the dispersed particles which promote strong adhesion characteristics to the particles and allowed the ethylene oxide component of the nonionic surfactant to effectively stabilise the droplets through steric stabilisation and helped reduce interfacial tension between the aqueous phase and non-aqueous phases. This is also thought to help to promote fine particle size.

It is thought that the choice of anionic surfactant provides for an even distribution of low level charge sufficient to assist stabilisation of the emulsion particles but not high enough to affect viscosity of the emulsion. It is for the above reasons that the combination of the two anionic and nonionic surfactants described above are thought to pack together at the interface and by so doing stabilise the emulsion droplets. Preferred anionic surfactants are calcium dodecyl benzene sulphonate, metal and amine salts of fatty acids (especially linoleic

TABLE 1

| Surfactant System Nonionic Type | % | Ionic Type | % | % Phasing after 2 weeks | Presence of Crystalization | Common Particle Size Range (um) | Colour | Dispersability in Water |
|---|---|---|---|---|---|---|---|---|
| Fatty $C_{17}$ alcohol/ 6 ethylene oxide | 80 | Vinsol Resin | 20 | 20 | — | Large drops >100 | Dark Brown | Very Poor |
| Fatty $C_{17}$ alcohol/ 6 ethylene oxide | 89 | Vinsol Resin | 20 | 6 | 2 weeks crystals throughout | 1–40 | Dark Brown | Poor |
| Medium chain alkyl phenol propoxylate/ ethoxylate | 40 | Calcium Dodecyl Benzene Sulphonate | 60 | 0 | — | <1 | Pale Brown | Excellent |
| Medium chain alkyl phenol propoxylate/ ethoxylate | 50 | Calcium Dodecyl Benzene Sulphonate | 50 | 0 | — | <1 | Pale Brown | Excellent |
| $C_{16}$ fatty amine/ 5 ethylene oxide | 50 | Tall Oil Fatty Acid + NaOH | 50 | 0 | — | 2–20 | Dark Brown | Good | and oleic), resin acids and high molecular weight polyacrylic acid stabilisers.

Above-mentioned blends of anionic and nonionic surfactants, albeit at varying ratios were found to be efficient for synthesis of the following emulsions:
1. trifluralin in abietic acid together with volatile and non volatile solvents.
2. chlorpyrifos in abietic acid and in resin based on the condensation of glycerol and abietic acid, together with volatile and non-volatile solvents.
3. metolachlor in bitumen, together with volatile and non-volatile solvents.

Typically the particle size of the disperse phase is less than 50 microns diameter and more usually less than 10 microns and even more usually less than 5 microns diameter. The formulations may also comprise one or more solvents for the active ingredient. Such solvents may be volatile, eg xylene and Solvesso 100. Solvesso 150 or Solvesso 200 and 1,1,1 tricholoroethane, or non-volatile such as paraffin or oleic acid or water-immiscible liquids with ester functionality. Solvesso 100, 150 and 200 are proprietary high aromatic volatile hydrocarbon solvents having different boiling point ranges. Solvesso is a trademark of Shell Australia. Examples of non-volatile liquids are esters of phthalic acid and of other fatty acids e.g. oleic acid and of abietic acid, and oligomeric and polymeric condensates of di-acids such as condensates of adipic acid and polyethylene glycol. The preferred esters are lower alkyl esters of oleic and abietic acid and the most preferred are methyl oleate and ethyl oleate. The above-mentioned blends of surfactants (at various ratios) were also found useful for non-bitumen emulsions.

The relative proportions of the viscous oil, active ingredient, surfactants, and solvents if present, are important to the working of the invention. The insoluble phase, being the combination of viscous oil and active is 10–80% w/w of the composition, more preferably 30–75% and most preferably 50–70%. It should be noted however that these percentages relate to compositions in the form that they are manufactured and transported. Clearly the lower the concentration of water present in the composition the more cost efficient are transport and packaging costs. In the most preferred compositions the water level is less than 30% by weight. However, compositions of the present invention may be diluted by the applicator of the formulation by typically 30 parts of water to 1 part of controlled release formulation.

The active ingredient is selected from the range of agricultural chemicals consisting of herbicides, fungicides, nematicides and insecticides. Preferably the active ingredient has a melting point less than 140° C. more preferably less than 100° C. and most preferably <80° C.

Especially preferred herbicides are the dinitroaniline class, particularly trifluralin and the chloroacetanilide class, particularly metolachlor. Preferred insecticides are the organophosphate class, particularly chlorpyrifos. In the compositions of the present invention the preferred levels of active are 3–70% w/w and most preferably 10–55%.

The volatile solvent e.g. Solvesso 150 is used up to 50% w/w more preferably up to 35% w/w and most preferably up to 25% w/w of the composition.

The non-volatile solvent is preferably a water insoluble liquid having ester functionality, e.g. phthalate di-esters or polyesters comprising adipic acid residues. More preferably the non-volatile solvent is selected from the group consisting lower alkyl esters of fatty acids or abietic acid, particularly methyl and ethyl esters.

Preferably the non-volatile solvent is used up to 40% w/w, more preferably up to 20% and most preferably up to 12%.

The aqueous phase of the formulation may contain additives to control the rheology and cold temperature storage properties of the dispersion. Examples of such additives are polyhydric alcohols such as glycerol, ethylene glycol, propylene glycol, sorbitol, polyethylene glycol and polypropylene glycol, Aqueous dispersions of the present invention are generally prepared by preparing a homogenous blend of the active ingredient and the viscous oil together with the water insoluble solvents if present. Usually heating these components to approximately 80°–90° C. facilitates the preparation of the blend. The surfactants, water soluble solvents and modifiers are dissolved in water by heating, preferably to 70°–90° C. to provide an aqueous phase. The aqueous phase is then added to under high shear conditions to the oil phase, or vice vera.

The invention will be further described by reference examples of preferred embodiments in which the compositions are expressed as part by weight.

BRIEF DESCRIPTION Of THE DRAWING

The accompanying drawings are graphs illustrating the results of experiments described in the following examples, which illte the invention.

EXAMPLE 1

FORMULATION A

BENEFIT OF FORMULATION: REDUCED PHYTOTOXICITY TO WHEAT

MATERIALS

Figure 1:
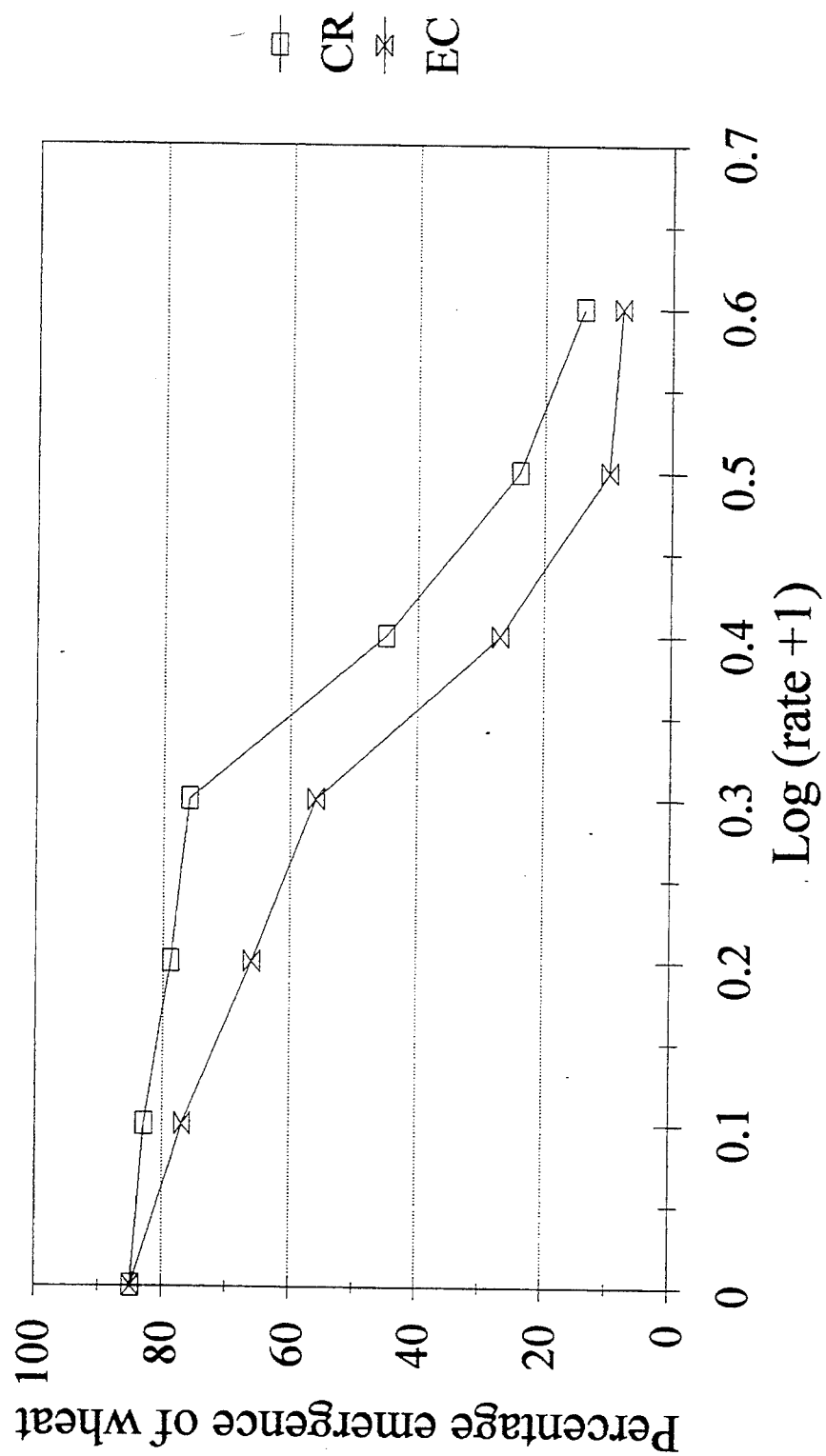
FIG. 1 relates to Example 1,
FIGS. 2a and 2b relate to Example 2,
FIGS. 3a and 3b relate to Example 3,
FIGS. 4a and 4b relate to Example 4,
FIGS. 5a and 5b relate to Example 7,
FIG. 6 relates to Example 8,
FIG. 7 relates to Example 9,
FIGS. 8a and 8b relate to Example 10,
FIGS. 9a and 9b relate to Example II,
FIG. 10 relates to Example 13,
FIG. II relates to Example 14,
FIGS. 12a and 12b relate to Example 15.

The viscous oil used as the matrix was bitumen of type C170(free of propane-deasphalted tar), This bitumen is defined in the Australian Standard AS2341, entitled "Properties of Residual Bitumens for Pavements".

Trifluralin (technical material) was supplied by Nufarm Pry Ltd, Pipe Road, Laverton, Victoria, Australia.

One of the surfactants used to form and stabilise the bituminous dispersion was calcium dodecyl benzene sulphonate (CaDDBS, 68% in butanol) as supplied by Nufarm Pty Ltd under the trademark Dobenz CA. This surfactant has a HLB of II±1. The non-ionic surfactant* is a medium chain length alkyl polyoxypropylene polyoxyethylene surfactant, having a HLB of 16.

METHOD OF FORMULATION OF DISPERSION

| a. Oil Phase | Trifluralin | 144 |
|---|---|---|
| | Bitumen C170 | 264 |

|   |   | Xylene | 72 |
|---|---|---|---|
|   |   | Dobenz CA | 16 |
|   |   | Non-ionic surfactant* | 16 |
| b. | Aqueous Phase | Water | 1,120 |

The oil phase components were heated together in a 1 liter container with mixing and the temperature was allowed to rise to 100° C. The container was periodically weighed and xylene lost by evaporation was replaced. When the oil phase was homogenous, it was poured into the water phase (water temperature 85° C.), which was contained in a 2 liter container. Throughout the addition of oil phase to water phase, the system was agitated using a Silverson L4R high shear mixer, with an emulsor screen attached. After 5 minutes the emulsion was cooled to 40° C. using an ice bath.

BIOASSAY PROTOCOL (PHYTOTOXICITY)

The bioassay protocol for the determination of phytotoxicity of the formulation was as follows.

Punnets (140×85×50 mm³) were filled with 500 g of soil, previously prepared to a standard moisture content depending on the soil type. This moisture was 11% for an acidic sandy loam, as typical of Wonwondah, Victoria, Australia. The soil moisture was 19% for a medium grey clay as typical of Dooen, Victoria, Australia, and was 11% for an alkaline sandy loam, as typical of the Mallee, Victoria, Australia. The punnets were sprayed with trifluralin formulations at a range of rates spanning 0–1,500 g trifluralin/ha through a laboratory boom sprayer. The boom passes over the punnets at 6 km/hr and delivers the water plus herbicidal formulation at 64 liters/ha through spraying systems (R) nozzles 11001 at 200 kPa.

Immediately after spraying, the soil in each punnet was mixed thoroughly in individual plastic bags and then returned to the punnets, and sown to wheat. The punnets were then transferred to a glasshouse where they were maintained at 16° C. and 24° C. for 8 and 16 hours respectively, for 10 days, being watered daily to avoid moisture stress.

The effect of the herbicide was assessed 10 days after spraying by determining the percentage of wheat seedlings which had emerged from the treated soil. A dose versus response curve was obtained for each formulation by fitting a line through the means of each of the six replicates. Formulations were deemed to have improved crop safety if substantially more wheat seedlings had emerged at any given application rate than from the standard emulsifiable concentrate formulation of trifluralin (40% active by weight).

RESULTS OF EXAMPLE 1

The results are tabulated in Table 2 and graphed in FIG. 1.

It is apparent from FIG. 1 that in the Mallee soil type used, the use of Formulation A led to substantially higher emergence of wheat seedlings compared to the EC (emulsifiable concentrate, 40% actives) which is the standard formulation supplied by Nufarm Australia). This result demonstrates that Formulation A has significantly lower phytotoxicity to wheat.

TABLE 2

PHYTOTOXICITY: EMERGENCE OF WHEAT VERSUS RATE (MALLEE SOIL) - EC VERSUS FORMULATION A

| Rate (l/ha) | Log (rate +) | % Emergence | |
|---|---|---|---|
| | | EC | Formulation A |
| 0 | 0 | 86 | 86 |
| 1.0 | 0.3 | 53 | 75 |
| 2.0 | 0.48 | 10 | 28 |
| 3.0 | 0.6 | 5 | 10 |

EXAMPLE 2

TRIFLURALIN CONTROLLED RELEASE FORMULATION B

BENEFIT OF FORMULATION: REDUCED PHYTOXICITY TO WHEAT

MATERIALS AND METHOD OF FORMULATION OF DISPERSION

The oil phase of the formulation consisted of:

| Trifluralin | 144 |
|---|---|
| Bitumen C170 | 68 |
| Xylene | 72 |
| Di-isodecyl phthalate | 96 |
| Nonionic surfactant* | 24 |
| Dobenz CA | 16 |

The water phase consisted of water 1120 parts by weight.

The method of preparing the dispersion was the same as for Example 1.

*see Example 1

BIOASSAY PROTOCOL (PHYTOTOXICITY): As for Example 1.

RESULTS OF EXAMPLE 2

Figure 2A:
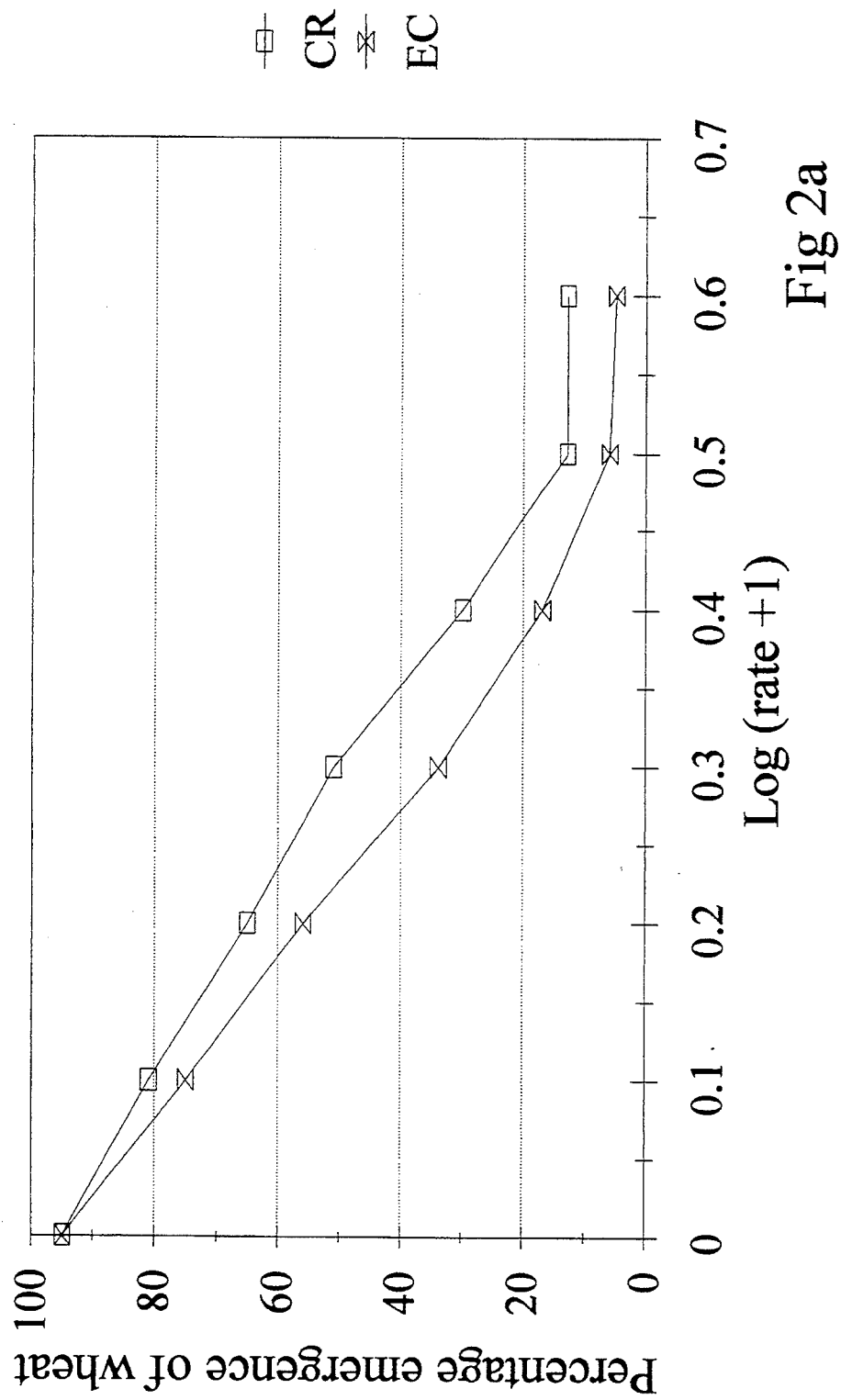
Figure 2B:
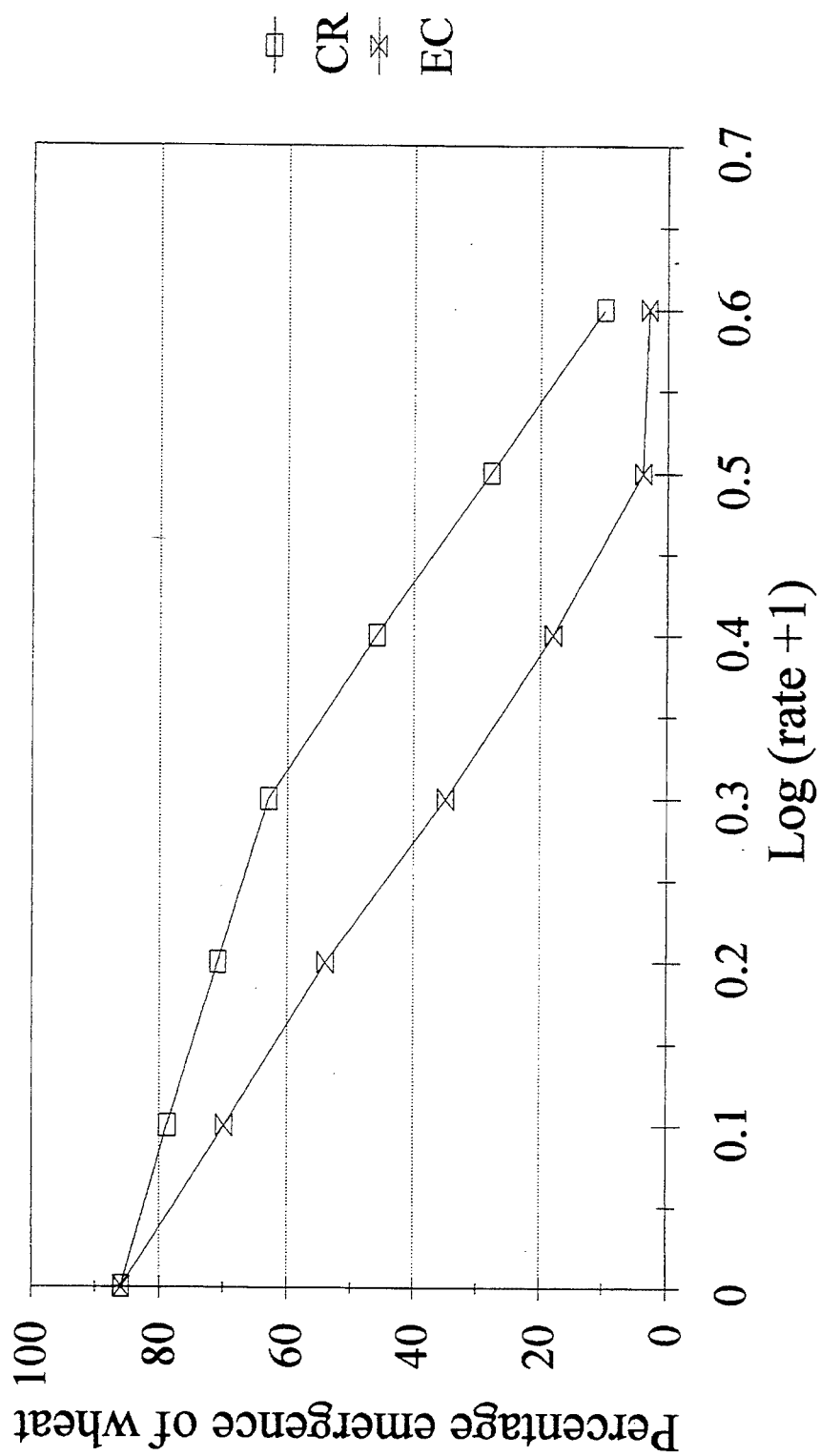

The results are tabulated in Tables 3a and 3b and graphed in FIGS. 2a and 2b.

It is apparent from FIGS. 2a and 2b that on both soil types studied the use of formulation B led to a substantially higher emergence of wheat seedlings compared to the EC at most application rates. This result demonstrates that Formulation B is significantly less phytotoxic to wheat.

TABLE 3a

PHYTOTOXICITY: EMERGENCE OF WHEAT VERSUS RATE (DOOEN SOIL) - EC VERSUS FORMULATION B

| Rate (l/ha) | Log (rate + 1) | % Emergence | |
|---|---|---|---|
| | | EC | Formulation B |
| 0 | 0 | 97 | 97 |
| 1.0 | 0.3 | 33 | 44 |
| 2.0 | 0.48 | 8 | 12 |
| 3.0 | 0.6 | 5 | 11 |

TABLE 3b

PHYTOTOXICITY: EMERGENCE OF WHEAT VERSUS RATE (MALLEE SOIL) - EC VERSUS FORMULATION B

| Rate (l/ha) | Log (rate + 1) | % Emergence | |
|---|---|---|---|
| | | EC | Formulation B |
| 0 | 0 | 86 | 86 |
| 1.0 | 0.3 | 35 | 62 |
| 2.0 | 0.48 | 3 | 33 |

TABLE 3b-continued

PHYTOTOXICITY: EMERGENCE OF WHEAT
VERSUS RATE (MALLEE SOIL) -
EC VERSUS FORMULATION B

| Rate (l/ha) | Log (rate + 1) | % Emergence | |
|---|---|---|---|
| | | EC | Formulation B |
| 3.0 | 0.6 | 3 | 9 |

EXAMPLE 3

TRIFLURALIN CONTROLLED RELEASE FORMULATION

BENEFIT OF FORMULATION: Reduced loss of trifluralin vapour to the atmosphere.

This example uses the same formulation as Example 2. but shows a different benefit of the formulation.

BIOASSAY PROTOCOL (VOLATILE LOSS OF ACTIVE)

The bioassay protocol for the determination of efficacy of the trifluralin formulations was as follows:

Soil was air dried and brought to a given level of water by weight (see bioassay protocol: phytotoxicity). The soil was placed into containers of dimension 85 mm×140 mm×50 mm (depth) and the containers of soil were sprayed at rates of formulation in the range 0–1.5 liters/hectare of trifluralin emulsifiable concentrate. The standard emulsifiable concentrate formulation contained 40% trifluralin active. A spray volume of 60 liters/hectare of water was used, and the dilute formulation were sprayed through Spraying System nozzles of type 11003 using 200 kilopascals of air pressure. Ambient temperature was 30°±3° C.

The sprayed containers were treated in two ways:
a. Soil was immediately mixed thoroughly after spraying to effect instant and complete incorporation of active, and returned to the container.
b. Sprayed soil was left for 48 hours, then mixed as above.

The treated soil portions were bioassayed for trifluralin according to the following protocol.

Soil portions were sown at 24 hours after spraying with 20 seeds of annual ryegrass (lollium rigidum) to a depth of 1 cm. The samples were kept at 18°–22° C. in a glasshouse for 10 days, and were watered twice daily. The results were obtained by calculating the percentage emergence from each container of soil.

The results are tabulated and are graphed using points which represent the mean value of six duplicates. The graphs are presented as % emergence vs $\log_{10}$ (dose+1). The numerical value for the dose is in units of liters per hectare equivalent of trifluralin emulsifiable concentrate.

In general, efficacy results for controlled release formulations are compared with efficacy results for the emulsifiable concentrate standard formulation sprayed at the same time.

The difference between the dose response curves corresponding to treatment (a) (immediate incorporation), and (b) (incorporation at t=48 hours) was taken to be related to the extent of volatile loss of active. A decrease in this difference would indicate reduced volatile loss.

RESULTS OF EXAMPLE 3

Figure 3A:
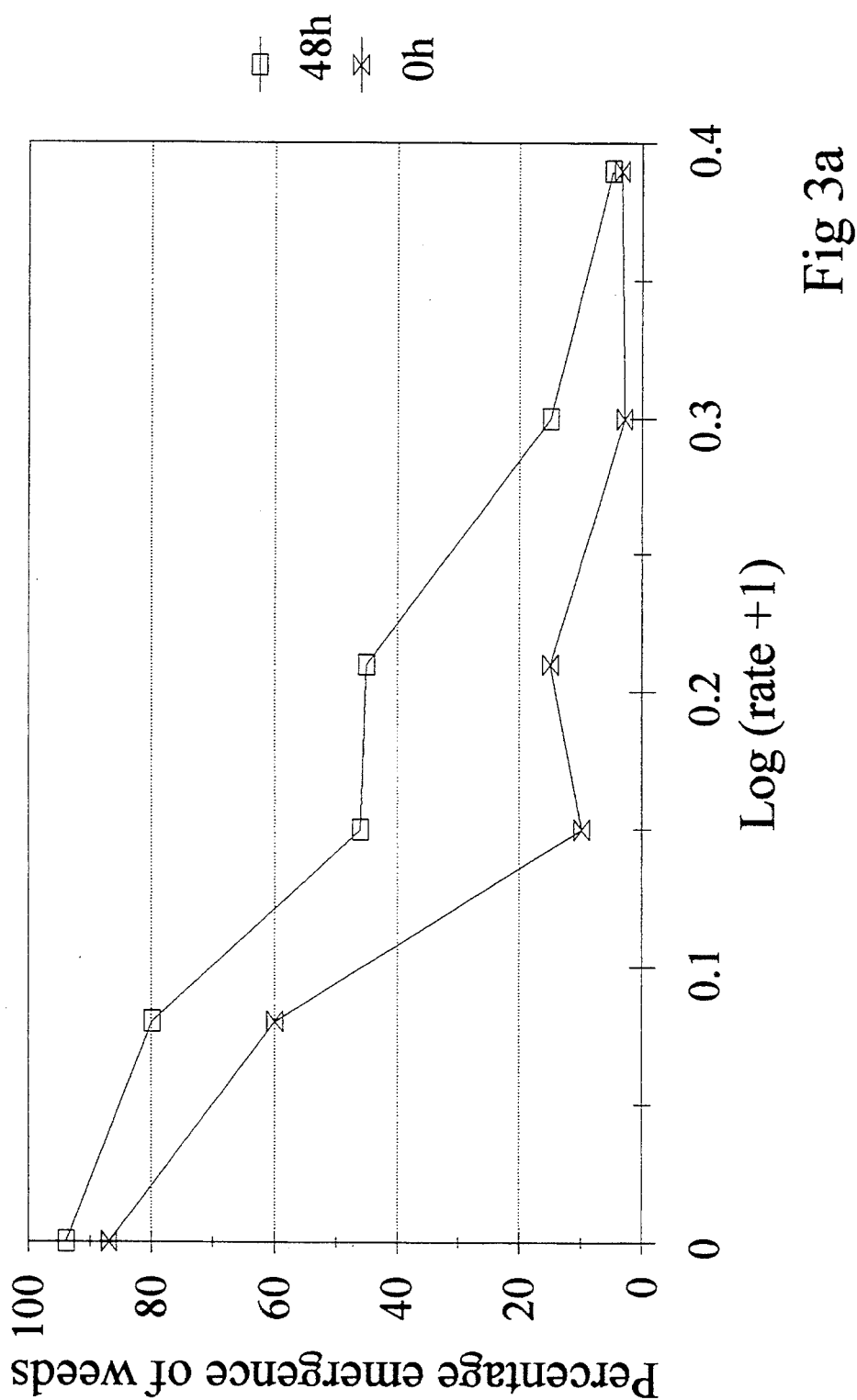
Figure 3B:
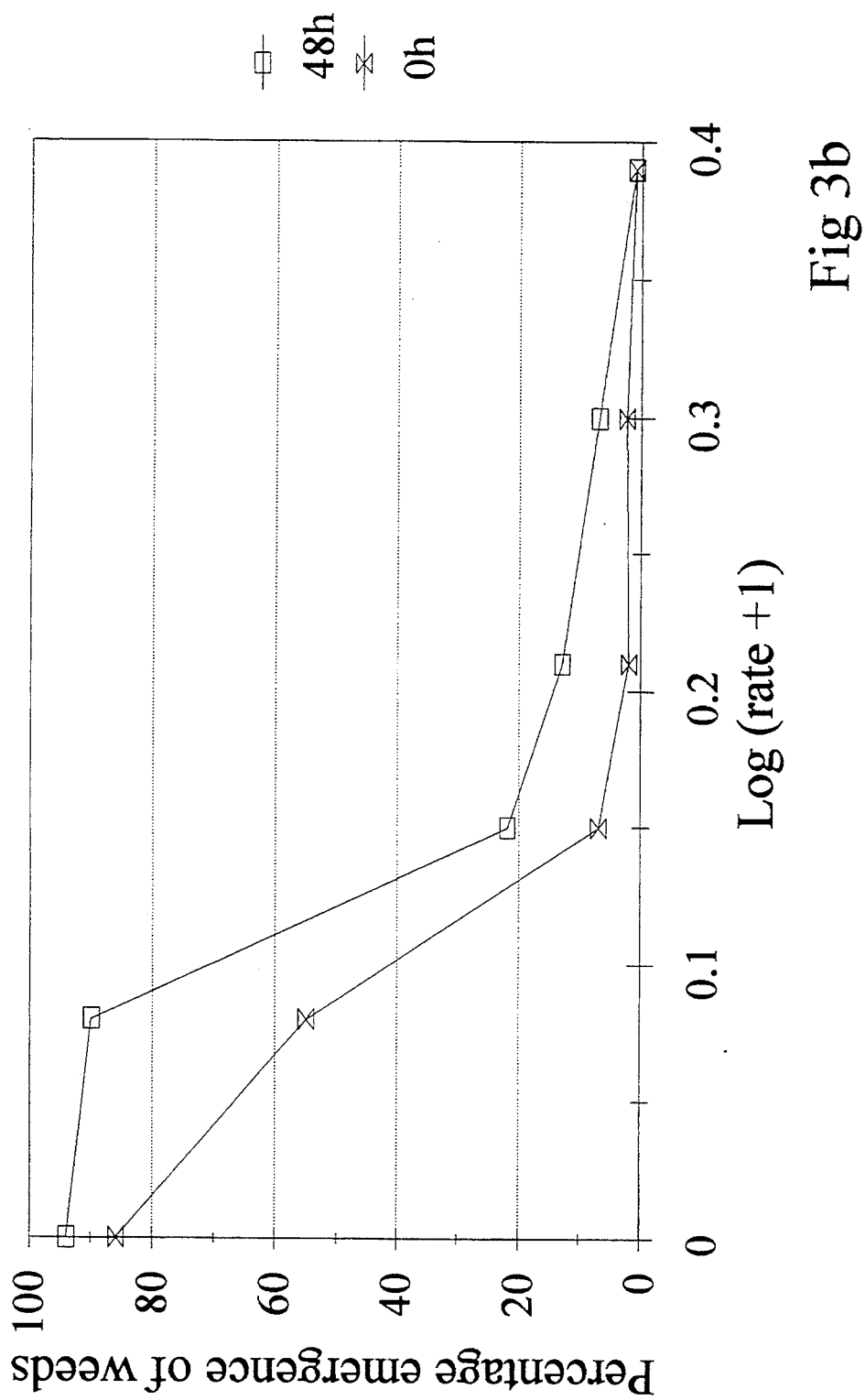

The results are tabulated in Tables 4a and 4b, and graphed in FIGS. 3a and 3b.

FIG. 3a shows the results for EC, which should be compared with FIG. 3b which gives the results for Formulation B. In all these experiments, the soil used was medium grey clay (Dooen).

It was concluded that the loss of efficacy caused by the delay in incorporation was significantly less when Formulation B was used.

TABLE 4a

VOLATILISATION EXPERIMENT: EMERGENCE
OF WEEDS VERSUS RATE DOOEN SOIL:
IMMEDIATE AND DELAYED
INCORPORATION - TRIFLURALIN EC

| Rate (l/ha) | Log (rate + 1) | % Emergence | |
|---|---|---|---|
| | | Imm. Inc | Del. Inc |
| 0 | 0 | 86 | 90 |
| 1.0 | 0.08 | 60 | 80 |
| 2.0 | 0.15 | 11 | 42 |
| 3.0 | 0.20 | 15 | 41 |
| 1.0 | 0.30 | 1 | 16 |
| 1.5 | 0.40 | 0 | 2 |

TABLE 4b

VOLATILISATION EXPERIMENT: EMERGENCE
OF WEEDS VERSUS RATE DOOEN SOIL:
IMMEDIATE AND DELAYED
INCORPORATION - FORMULATION B

| Rate (l/ha) | Log (Rate − 1) | % Emergence | |
|---|---|---|---|
| | | Immediate Inc. | Delayed Inc. |
| 0 | 0 | 88 | 90 |
| 0.2 | 0.08 | 55 | 90 |
| 0.4 | 0.15 | 5 | 20 |
| 0.6 | 0.20 | 1 | 14 |
| 1.0 | 0.30 | 0 | 5 |
| 1.5 | 0.40 | 0 | 1 |

EXAMPLE 4

TRIFLURALIN CONTROLLED RELEASE FORMULATION C

BENEFIT OF FORMULATION: REDUCED PHYTOTOXICITY TO WHEAT MATERIALS (SEE EXAMPLE 1)

METHOD OF FORMULATION OF DISPERSION C

The dispersion consisted of:

| Component | Parts w/w % |
|---|---|
| Oil Phase | |
| Trifluralin (technical grade) | 20.26 |
| Bitumen C170 PD Tar free | 35.80 |
| Xylene | 11.48 |
| Aqueous Phase | |
| Water | 24.65 |
| Dobenz CA | 2.09 |
| nonionic surfactant* (see Example I) | 1.39 |
| Glycerol | 4.33 |

The oil phase was prepared by blending the melted bitumen and trifluralin and xylene until homogenous at 90° C.

The aqueous phase was prepared by dissolving the components in the water at 80° C.

The oil phase was heated to 100° C. prior to emulsification. The aqueous phase (80° C.) was added to the oil phase and emulsified using a Silverson homogenizer with a 16 mm disintegrating head at 2/3 maximum speed for 2 minutes.

The resulting emulsion had a viscosity of 1500 cp. The droplet size of the emulsion was typically less than 2 um. After two months torage at ambient temperature there was no sign of trifluralin crystallization, droplet coalescence or emulsion deterioration as determined by techniques well known in the art.

Formulation C was the same as Formulation A in terms of matrix composition but the oil phase ratio percentage much higher.

BIOASSAY PROTOCOL (PHYTOTOXICITY): See Example 1

RESULTS OF EXAMPLE 4

Figure 4A:
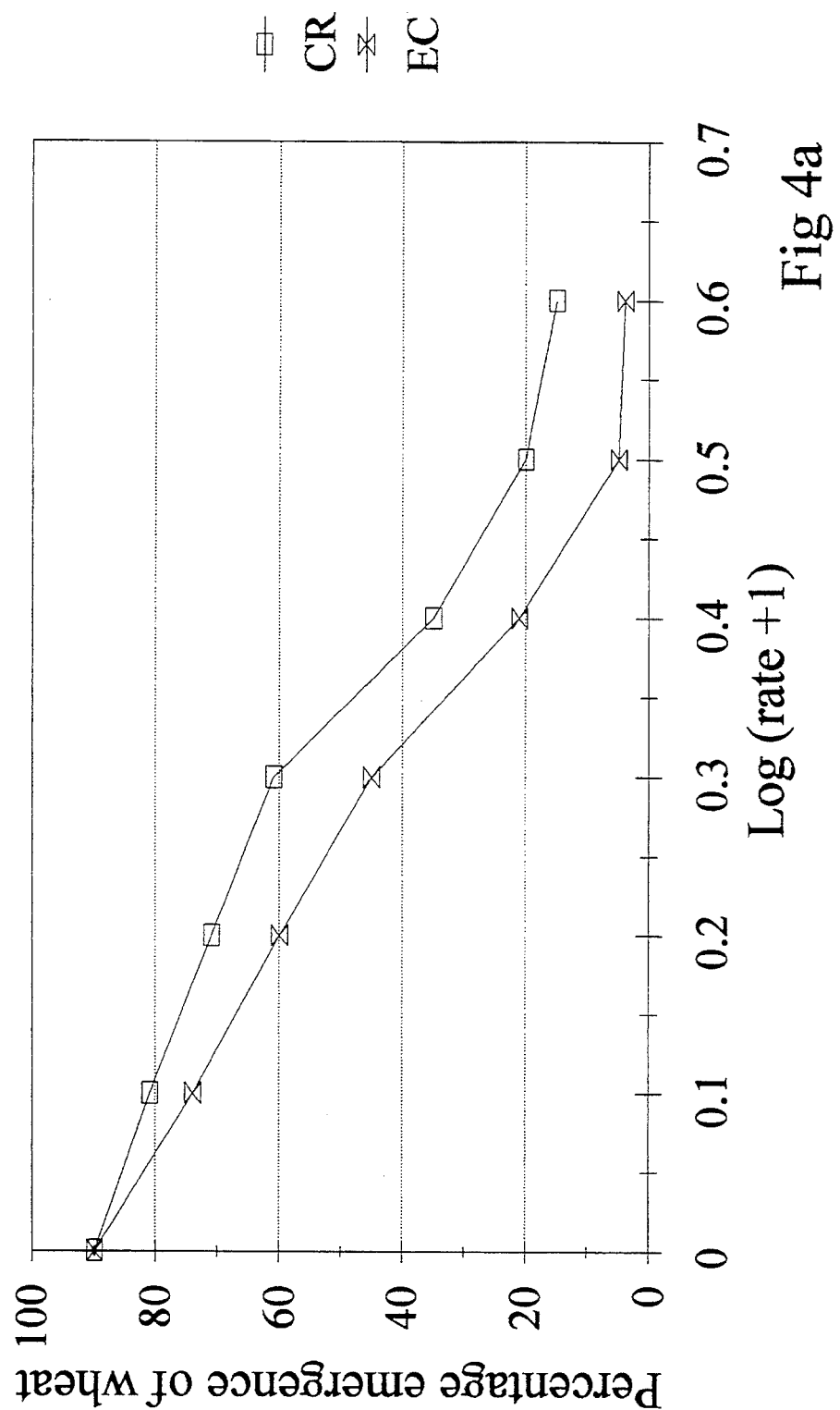
Figure 4B:
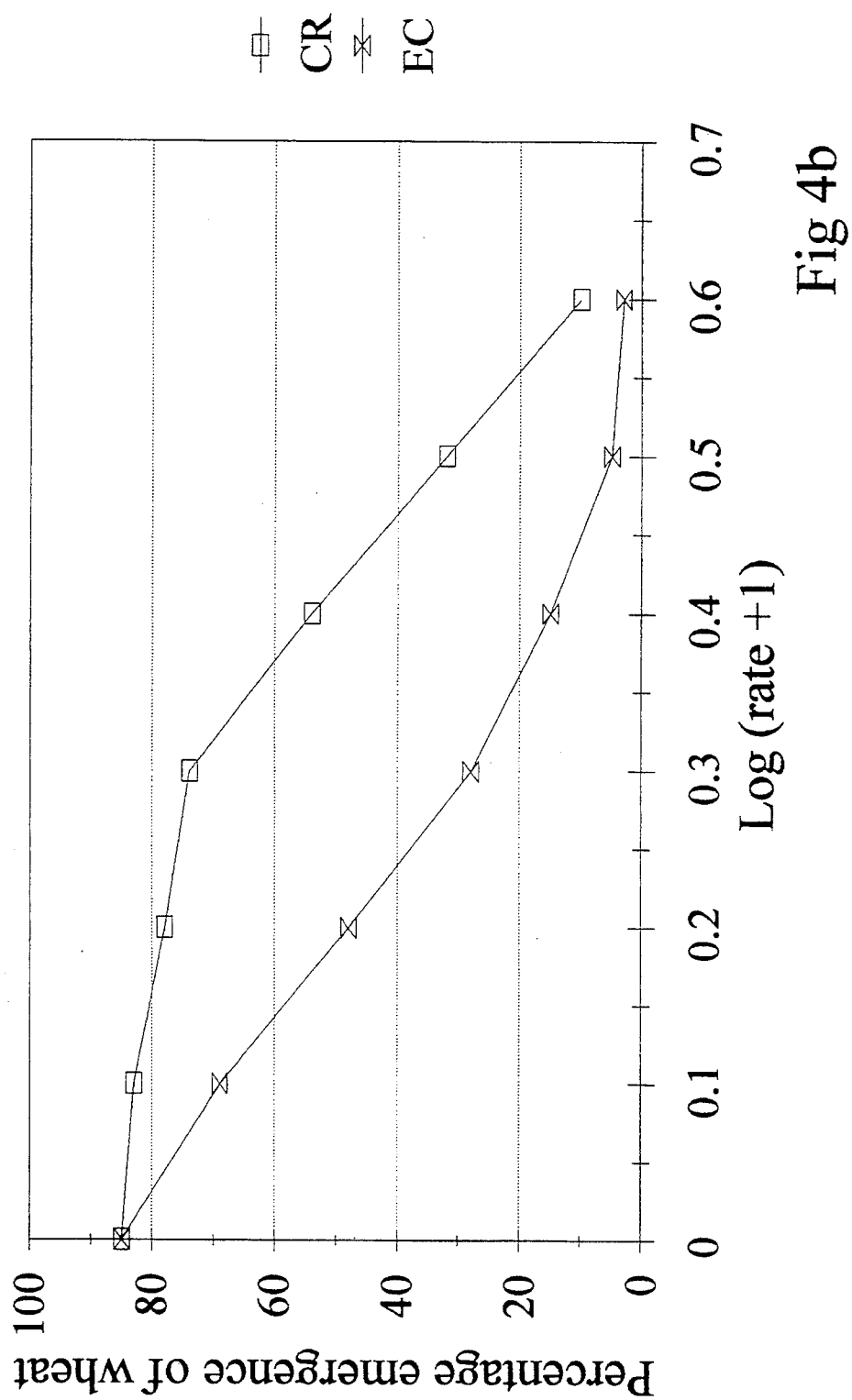

The results are tabulated in Tables 5a and 5b and are graphed in FIGS. 4a and 4b.

It is apparent from FIGS. 4a and 4b that on both soil types studied at Dooen and Mallee respectively, the use of Formulation C led to a higher emergence of wheat seedlings compared to the EC at most application rates. This demonstrates that Formulation C was significantly less phytotoxic to wheat.

TABLE 5a

PHYTOTOXICITY: EMERGENCE OF WHEAT VERSUS RATE DOOEN SOIL: EC VERSUS - FORMULATION C

| Rate (l/ha) | Log (rate + 1) | % Emergence EC | % Emergence Formulation C |
|---|---|---|---|
| 0 | 0 | 90 | 90 |
| 1.0 | 0.30 | 43 | 60 |
| 2.0 | 0.48 | 2 | 20 |
| 3.0 | 0.06 | 3 | 12 |

TABLE 5b

PHYTOTOXICITY: EMERGENCE OF WHEAT VERSUS RATE MALLEE SOIL: EC VERSUS - FORMULATION C

| Rate (l/ha) | Log (rate + 1) | % Emergence EC | % Emergence Formulation C |
|---|---|---|---|
| 0 | 0 | 88 | 88 |
| 1.0 | 0.30 | 29 | 73 |
| 2.0 | 0.48 | 5 | 39 |
| 3.0 | 0.06 | 2 | 10 |

EXAMPLE 5

An emulsion of the type suitable for use as a pre-emergent herbicide was prepared using the following components according to the procedure below.

| Component | Part w/w % |
|---|---|
| Oil Phase | |
| Trifluralin technical grade | 20.26 |
| Bitumen PD tar free | 29.29 |
| Xylene | 11.48 |
| Di-isodecyl phthalate | 6.51 |
| Aqueous Phase | |
| Water | 28.96 |
| Calcium dodecyl benzene sulphonate (68% active) | 2.10 |
| Non-ionic surfactant** | 1.40 |

The non-ionic surfactant** is an alkyl polyoxypropylene polyoxyethylene condensate where alkyl is $C_3$–$C_8$ the polyoxypropylene is 67–77 moles; and the polyoxyethylene is 70–80 moles.

The oil phase was prepared by blending the components at 90° C. until fluid and homogeneous and heating to 100° C. prior to emulsification.

The emulsifier was dissolved in the aqueous phase at 800° C.

The aqueous phase was added to the oil phase and emulsified using a Silverson homogenizer with a 16 mm disintegrating head at 2/3 maximum speed for 2 minutes.

The resulting emulsion had a viscosity of 1800 cp. The droplet size was typically less than 2 um. After one month storage at ambient temperature the emulsion showed no signs of trifluralin crystallization, droplet coalescence or deterioration as determined by techniques commonly employed in the art.

EXAMPLE 6

An emulsion suitable for use as a pre-emergent herbicide was prepared using the following components according to the procedure below.

| Component | | Part w/w % |
|---|---|---|
| Oil Phase | Trifluralin technical grade | 20.26 |
| | Bitumen C170 PD Tar free | 35.80 |
| | Xylene | 11.48 |
| Aqueous Phase | Water | 24.62 |
| | Calcium dodecyl benzene Sulphonate (68% active) | 1.755 |
| | Nonionic surfactant* (see Example 1) | 1.755 |
| | Glycerol | 4.34 |

The oil phase was heated to 100° C. prior to emulsification. The aqueous phase (at 80° C.) was added to the oil phase and emulsified using a Silverson homogenizer with a 16 mm disintegrating head for 2 minutes.

EXAMPLE 7

TRIFLURALIN, CONTROLLED RELEASE FORMULATION D. BENEFIT OF FORMULATION: INCREASED POTENCY OF TRIFLURALIN

MATERIALS

The oil phase of the formulation consisted of

| | |
|---|---|
| Trifluralin | 96 |
| Chinese Rosin (natural product substantially abietic acid ex China) | 72 |
| Solvesso 150 | 72 |
| Nonionic surfactant* (see Example 1) | 14 |
| Dobenz CA | 6 |

The water phase consisted of 560 parts.

METHOD OF FORMULATION Of DISPERSION D

Trifluralin and Chinese rosin were heated together until homogeneous at 100° C. and then solvesso 150 and Dobenz CA were added and stirred. This oil phase (90° C.) was added to water (90° C.) in the presence of high shear agitation provided by a Silverson L4R high shear mixer. Particle size was 1–3 microns.

BIOASSAY PROTOCOL: (As for volatile loss of active—see Example 3)

RESULTS OF EXAMPLE 7

Figure 5A:
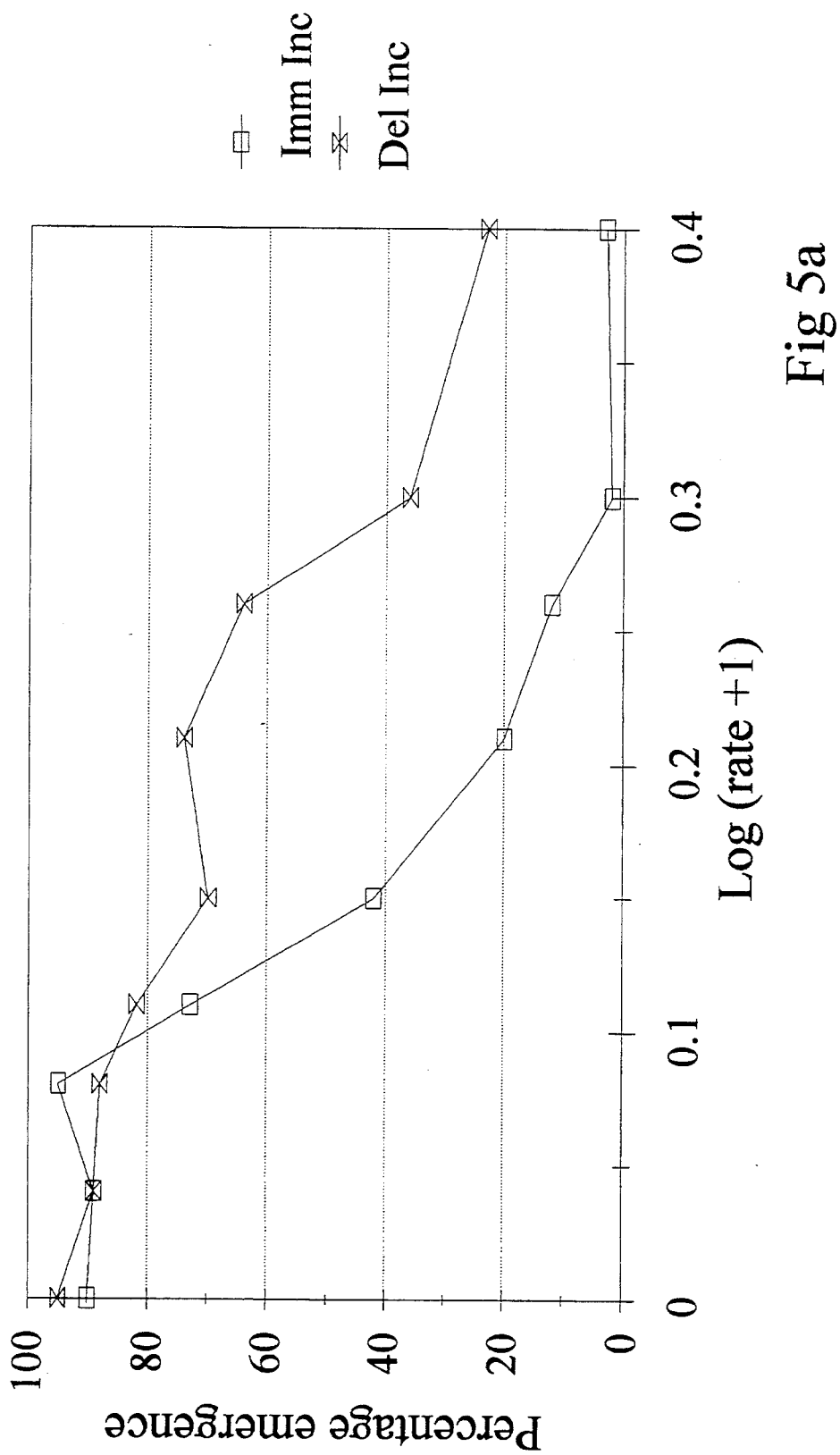
Figure 5B:
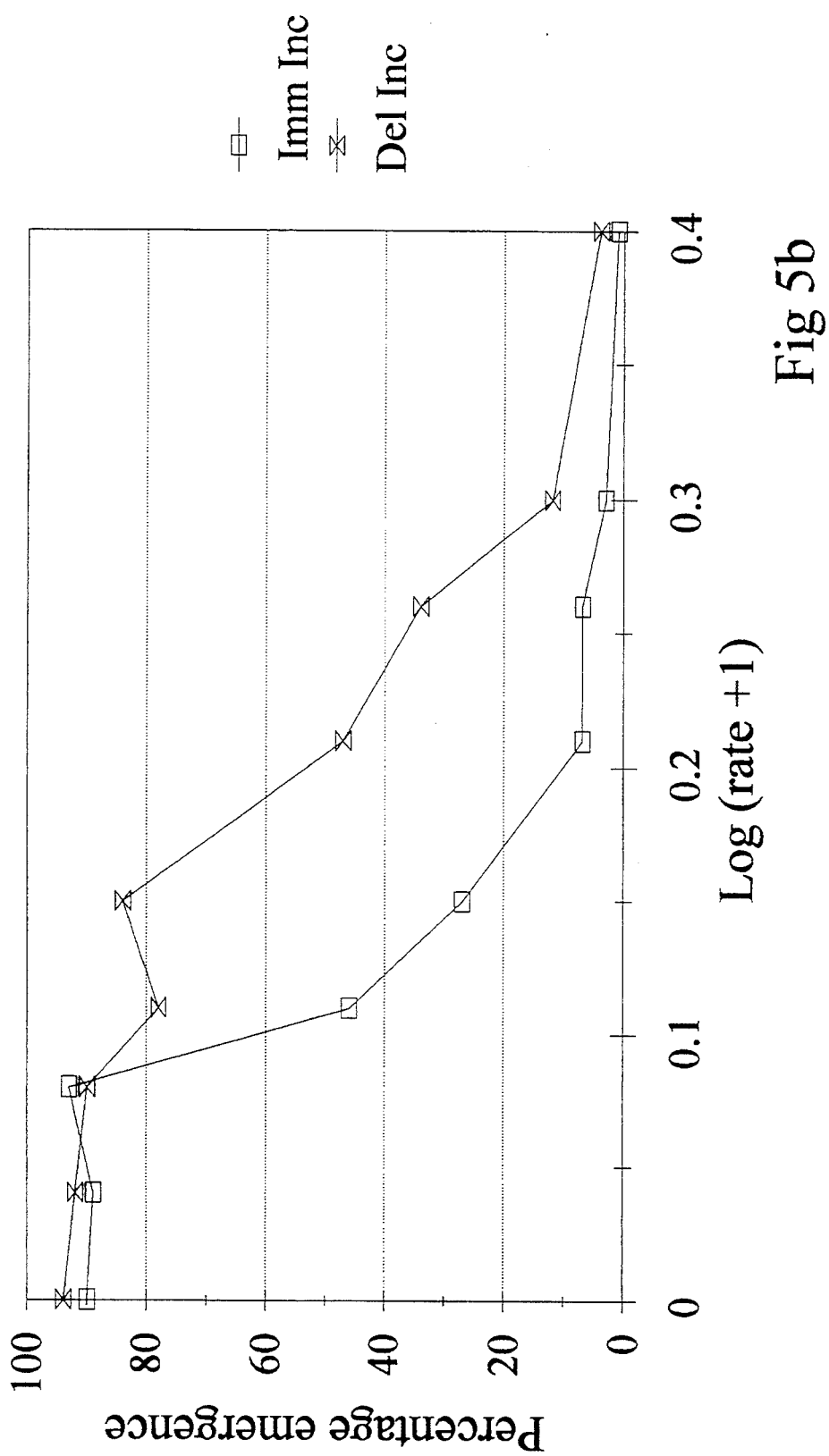

The results are tabulated in Tables 6(a), 6(b) and graphed in FIGS. 5(a) and 5(b). FIG. 5(a) shows the results for EC, which should be compared with FIG. 5(b) which gives the results for Formulation D. For all these experiments the soil used was an alkaline sandy loan as typical of the Mallee, Victoria, Australia.

It was concluded that Formulation D was significantly more potent than was the EC both under conditions of immediate and delayed incorporation.

TABLE 6 (a)

TRIFLURALIN EC
POTENCY EXPERIMENT - EMERGENCE
OF WEEDS ON RATE.
MALLEE SOIL. IMMEDIATE AND DELAYED
INCORPORATION.

| Rate (1/ha) | Log$_{10}$ (rate + 1) | % Emergence | |
|---|---|---|---|
| | | Imm. Inc. | Del. Inc. |
| 0 | 0 | 90 | 95 |
| 0.1 | 0.05 | 90 | 90 |
| 0.2 | 0.09 | 94 | 90 |
| 0.3 | 0.12 | 72 | 82 |
| 0.4 | 0.15 | 41 | 70 |
| 0.6 | 0.2 | 19 | 73 |
| 0.8 | 0.26 | 10 | 64 |
| 1 | 0.3 | 1 | 35 |
| 1.5 | 0.4 | 3 | 22 |

TABLE 6 (b)

TRIFLURALIN FORMULATION D.
POTENCY EXPERIMENT - EMERGENCE OF WEEDS
ON RATE. MALLEE SOIL.
IMMEDIATE AND DELAYED INCORPORATION.

| Rate (1/ha) EC Equivalent | Log$_{10}$ (rate + 1) | % Emergence | |
|---|---|---|---|
| | | Imm. Inc. | Del. Inc. |
| 0 | 0 | 90 | 95 |
| 0.1 | 0.05 | 89 | 92 |
| 0.2 | 0.09 | 92 | 90 |
| 0.3 | 0.12 | 47 | 78 |
| 0.4 | 0.15 | 28 | 84 |
| 0.6 | 0.2 | 8 | 48 |
| 0.8 | 0.26 | 8 | 33 |
| 1 | 0.3 | 3 | 10 |
| 1.5 | 0.4 | 1 | 3 |

EXAMPLE 8

TRIFLURALIN CONTROLLED RELEASE
FORMULATION E

BENEFIT OF FORMULATION: REDUCED
PHYTOTOXCITY TO WHEAT

MATERIALS AND METHOD OF FORMULATION OF DISPERSION E

The oil phase of the formulation consisted of

| Trifluralin | 96 |
|---|---|
| Chinese rosin | 48 |
| Solvesso 150 | 96 |
| Nonionic surfactant* | 14 |
| Dobenz CA | 6 |

The water phase consisted of 560 pans. The method used was as for Example 7.
*see Example 1
BIOASSAY PROTOCAL (PHYTOTOXITY) As for Example 1

RESULTS OF EXAMPLE 8

Figure 6:
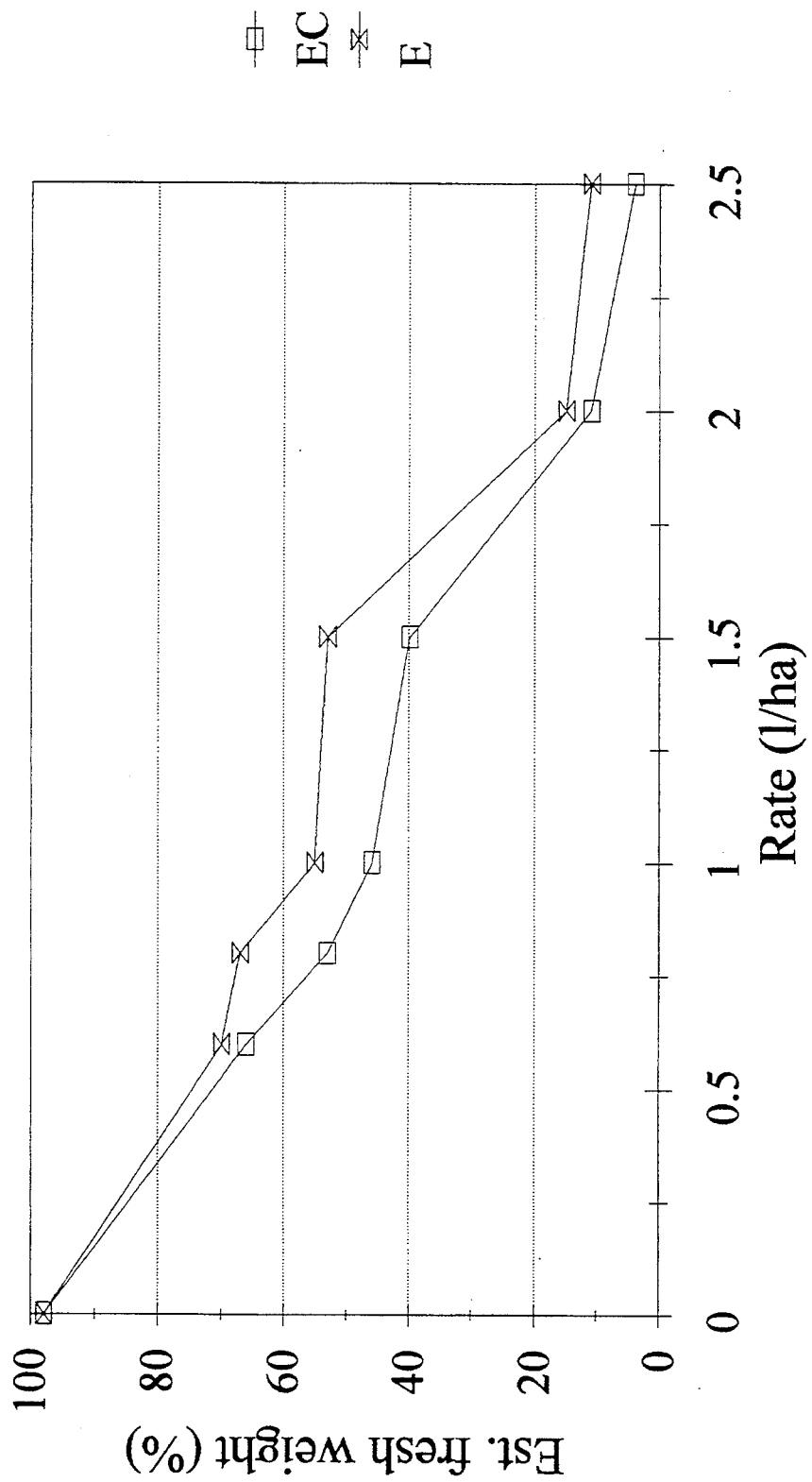

The results are tabulated in Table 7, which includes control data relating to EC, and are graphed in FIG. 6.

TABLE 7

PHYTOTOXCITY: EMERGENCE OF WHEAT
VESUS RATE
MALLEE SOIL - EC & TRIFLURALIN FORMULATION E

| Rate (1/ha) | Log$_{10}$ (rate + 1) | % Emergence | |
|---|---|---|---|
| | | EC | Formulation E |
| 0 | — | 98 | 98 |
| 0.6 | — | 65 | 69 |
| 0.8 | — | 52 | 66 |
| 1 | — | 47 | 55 |
| 1.5 | — | 40 | 51 |
| 2 | — | 12 | 12 |
| 2.5 | — | 6 | 9 |

It is apparent from FIG. 6 that the use of Formulation E on Mallee soil led to a substantially higher emergence of wheat seedlings compared to EC at most application rates. This result demonstrates that Formulation E is less phytotoxic to wheat.

EXAMPLE 9

TRIFLURALIN CONTROLLED RELEASE
FORMULATION F
BENEFIT OF FORMULATION: REDUCED
PHYTOTOXICITY TO WHEAT
MATERIALS AND METHOD OF FORMULATION OF
DISPERSION F

The oil phase of the formulation consisted of

| Trifluralin | 168 |
|---|---|
| Chinese Rosin | 144 |
| Estergum SA (glycerol ester of abietic acid, manufactured by Frankston Manufacturing Co., Victoria) | 48 |
| Solvesso 150 | 120 |
| Nonionic surfactant* (see Example 1) | 28 |
| Dobenz CA | 12 |

The water phase consisted of 1,120 parts. The method used was as for example 7.
BIOASSAY PROTOCOL (PHYTOTOXICITY) As for Example 1.

RESULTS OF EXAMPLE 9

Figure 7:
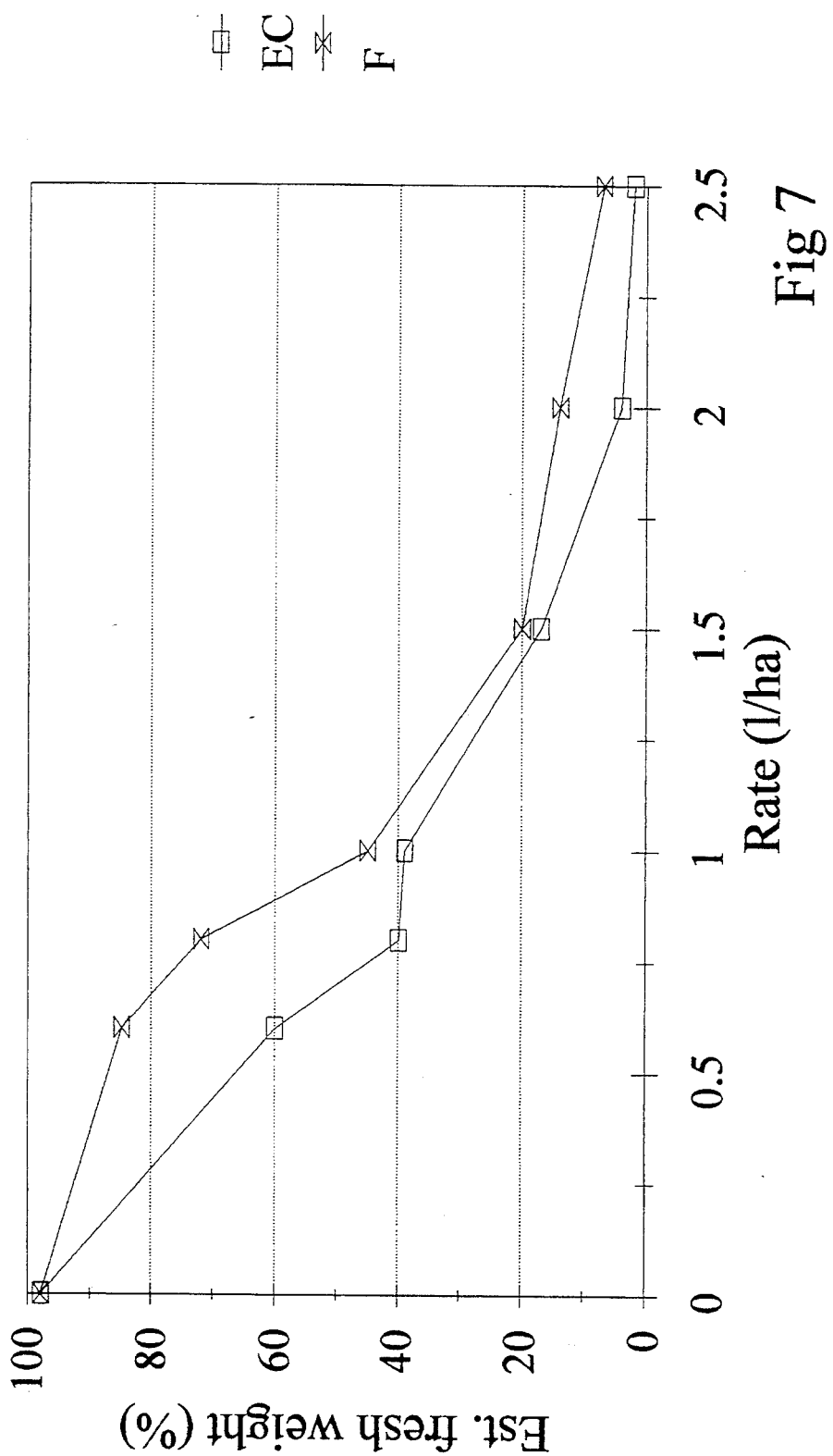

The results are tabulated in Table 8 which includes control data relating to EC, and are graphed in FIG. 7.

TABLE 8

PHYTOTOXCITY: EMERGENCE OF WHEAT
VESUS RATE
MALLEE SOIL - EC & TRIFLURALIN FORMULATION F

| Rate (1/ha) | Log$_{10}$ (rate + 1) | % Emergence | |
|---|---|---|---|
| | | EC | Formulation F |
| 0 | — | 98 | 98 |
| 0.6 | — | 62 | 84 |
| 0.8 | — | 42 | 72 |
| 1 | — | 39 | 46 |
| 1.5 | — | 18 | 21 |
| 2 | — | 3 | 16 |
| 2.5 | — | 2 | 8 |

It is apparent from FIG. 7 that the use of Formulation F on Mallee soil led to a higher emergence of wheat seedlings compared to EC at most application rates. This result demonstrates that Formulation F is less phytotoxic to wheat.

EXAMPLE 10

TRIFLURALIN CONTROLLED RELEASE FORMULATION G

BENEFIT OF FORMULATION; INCREASED POTENCY OF TRIFLURALIN

| Materials | |
|---|---|
| Trifluralin | 120 |
| Chinese rosin | 72 |
| Solvess 150 | 48 |
| Nonionic surfactant* | 14 |
| Dobenz CA | 6 |

The water phase consisted of 560 parts. The method was as for Example 7.

* see Example 1

BIOASSAY PROTOCOL (AS FOR VOLATILE LOSS OF ACTIVE—SEE EXAMPLE 3)

RESULTS OF EXAMPLE 10

Figure 8A:
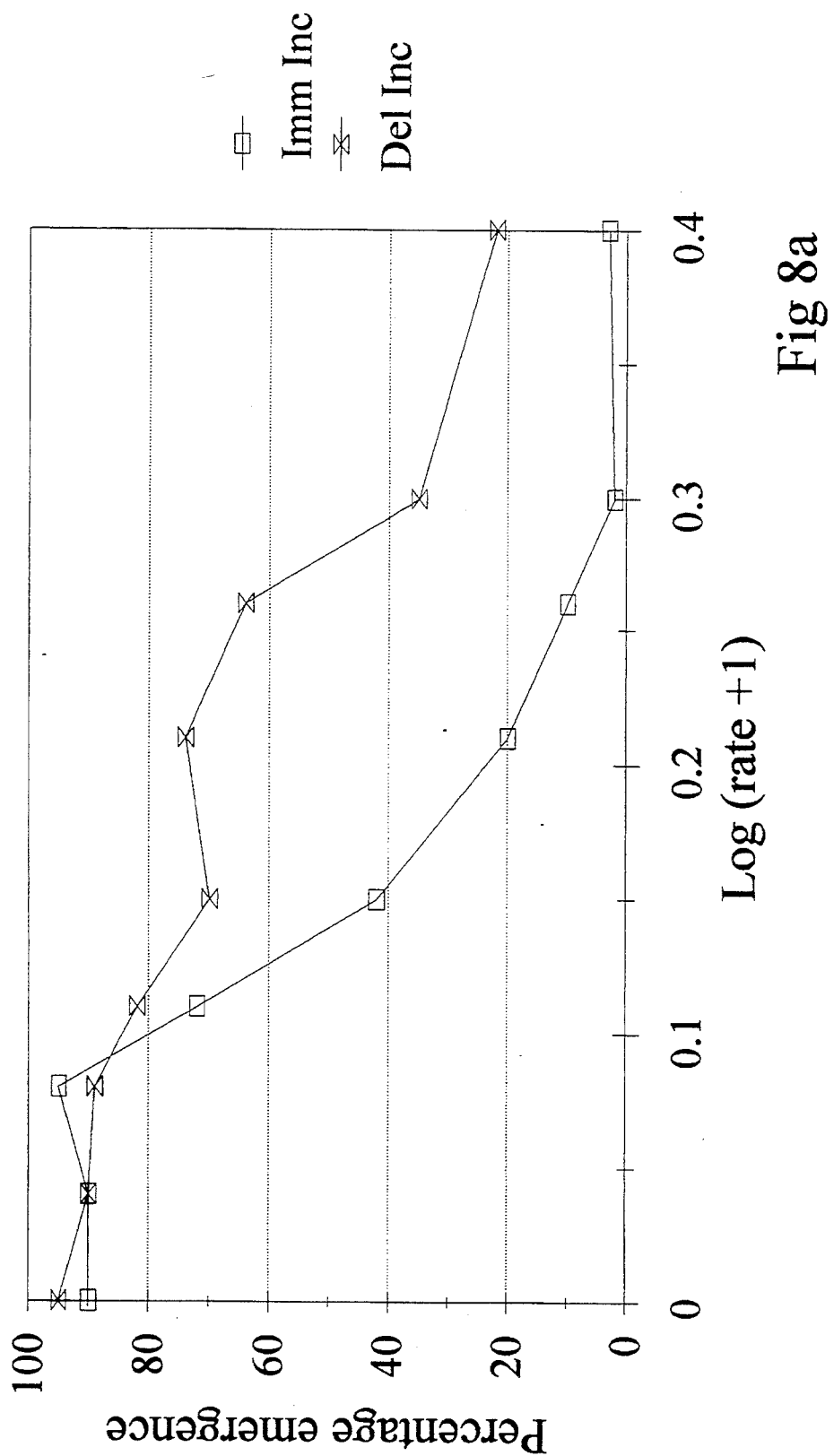
Figure 8B:
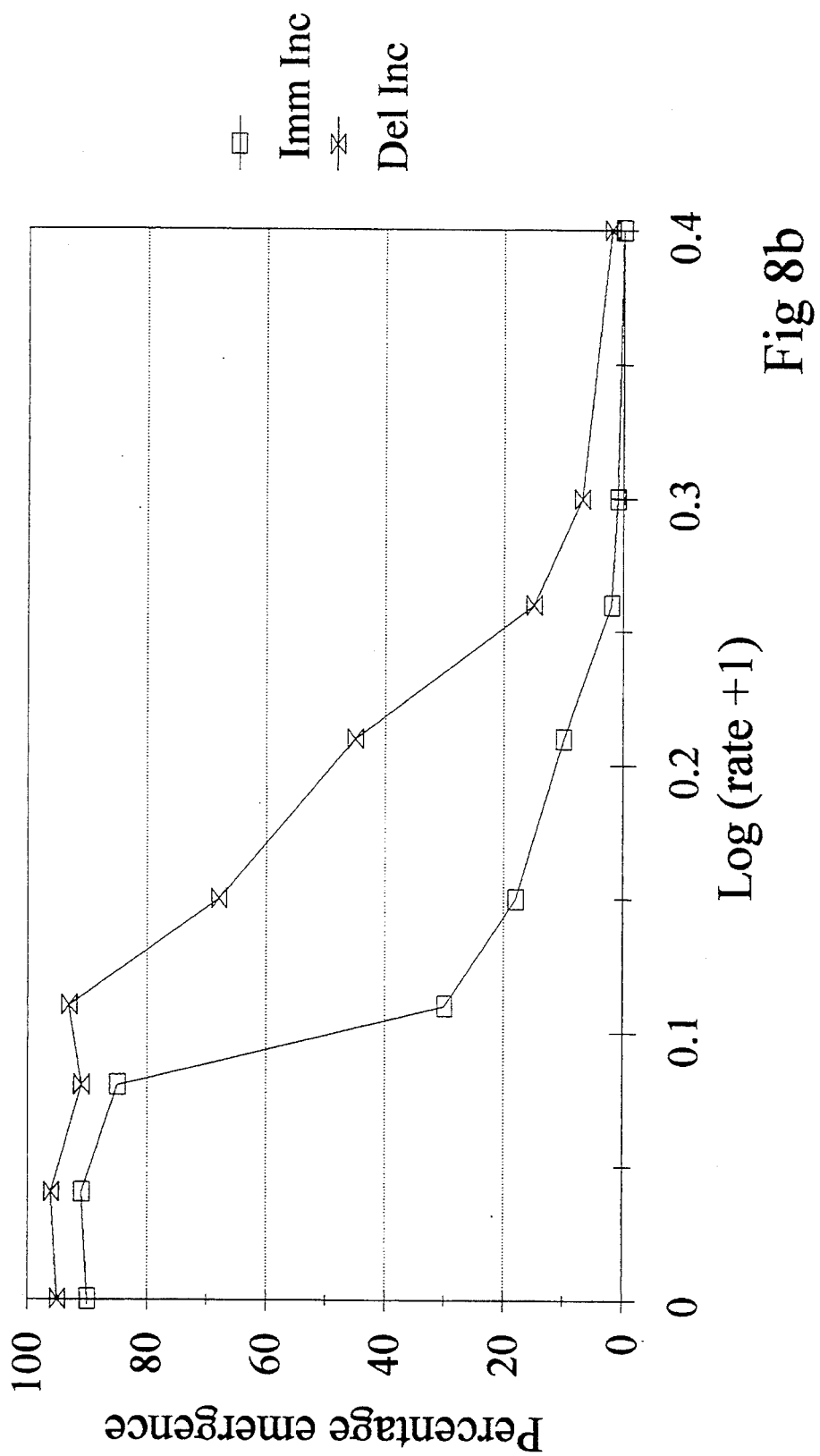

The results are tabulated in Tables 9(a), 9(b) and graphed in FIGS. 8(a) and 8(b). FIG. 8(a) shows the results for EC which should be compared with FIG. 8(b) which gives the results for Formulation G. Mallee soil was used in all experiments. It was concluded that Formulation G was significantly more potent than was the EC both under conditions of immediate and delayed incorporation.

TABLE 9 (a)

TRIFLURALIN EC (40% ACTIVE) POTENCY EXPERIMENT - EMERGENCE OF WEEDS VS RATE MALLEE SOIL. IMMEDIATE AND DELAYED IN CORPORATION

| | | % Emergence | |
|---|---|---|---|
| Rate 1/ha | $Log_{10}$ (rate + 1) | Imm. Inc. | Del. Inc. |
| 0 | 0 | 90 | 95 |
| 0.1 | 0.05 | 90 | 90 |
| 0.2 | 0.09 | 92 | 90 |
| 0.3 | 0.12 | 94 | 82 |
| 0.4 | 0.15 | 41 | 70 |
| 0.6 | 0.2 | 19 | 73 |
| 0.8 | 0.26 | 10 | 64 |
| 1 | 0.3 | 1 | 35 |
| 1.5 | 0.4 | 3 | 22 |

TABLE 9 (b)

TRIFLURALIN FORMULATION G POTENCY EXPERIMENT - EMERGENCE OF WEEDS VS RATE MALLEE SOIL. IMMEDIATE AND DELAYED INCORPORATION

| | | % Emergence | |
|---|---|---|---|
| Rate 1/ha | $Log_{10}$ (rate + 1) | Imm. Inc. | Del. Inc. |
| 0 | 0 | 90 | 95 |
| 0.1 | 0.05 | 91 | 96 |
| 0.2 | 0.09 | 86 | 91 |
| 0.3 | 0.12 | 30 | 93 |
| 0.4 | 0.15 | 19 | 69 |
| 0.6 | 0.2 | 10 | 46 |
| 0.8 | 0.26 | 2 | 15 |
| 1 | 0.3 | 1 | 7 |
| 1.5 | 0.4 | 0 | 3 |

EXAMPLE 11

TRIFLURALIN CONTROLLED RELEASE FORMULATION H

BENEFIT OF FORMULATION: INCREASED POTENCY OF TRIFLURALIN

MATERIALS

| Trifluralin | 192 |
|---|---|
| Chinese rosin | 48 |
| Solvess 150 | 240 |
| Nonionic surfactant* | 28 |
| Dobenz CA | 12 |

The water phase consisted of 1,120 parts. The method was as for Example 7.

* see Example 1

BIOSSAY PROTOCAL (AS FOR VOLATILE LOSS OF ACTIVE—SEE EXAMPLE 3)

RESULTS OF EXAMPLE 11

Figure 9A:
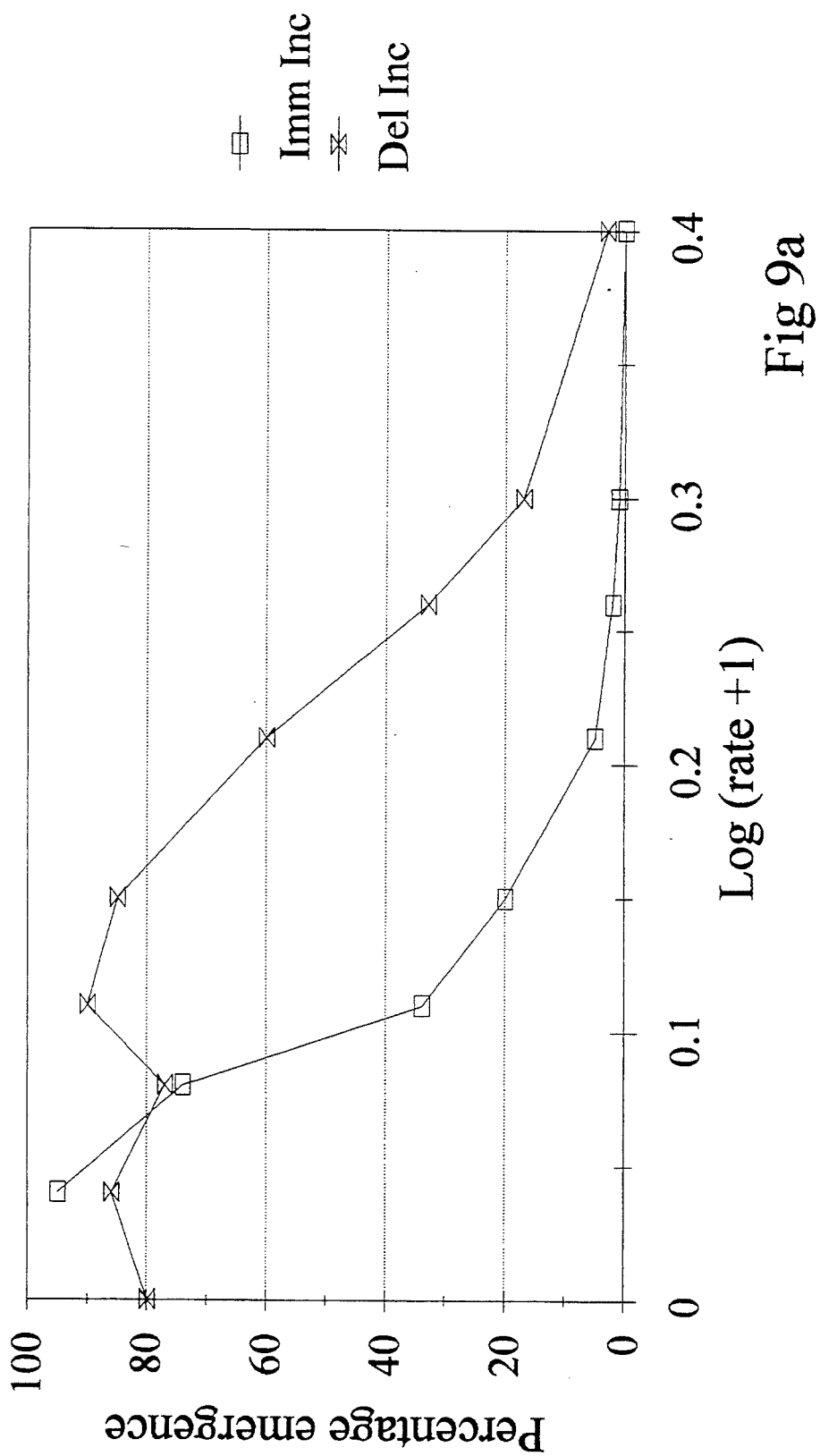
Figure 9B:
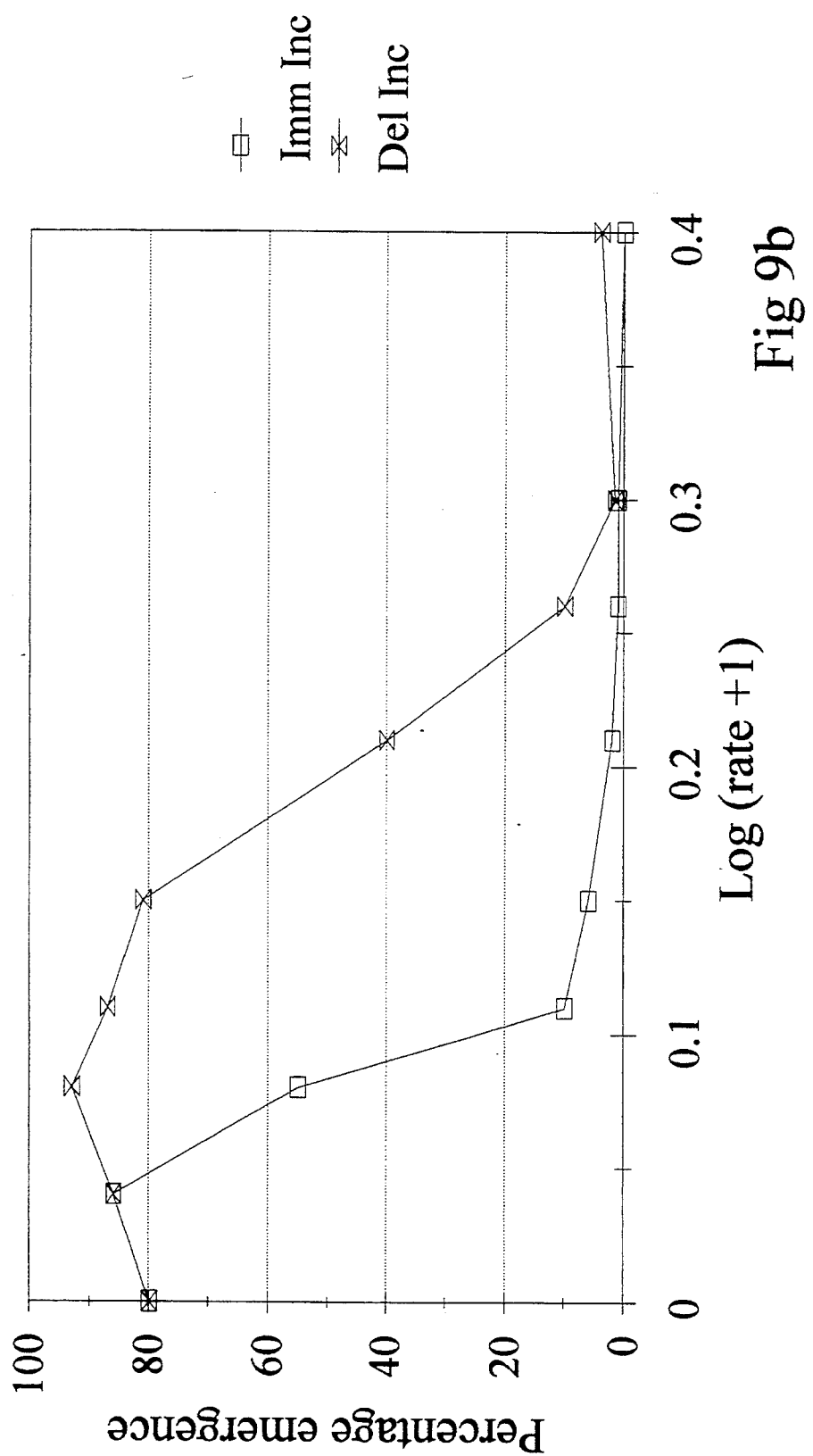

The results are tabulated in Tables 10(a), 10(b) and graphed in FIGS. 9(a) and 9(b). FIG. 11(a) shows the results for EC which should be compared with FIG. 9(b) which gives the results for Formulation H. It was concluded that formulation H was significantly more potent than was the EC.

TABLE 10 (a)

TRIFLURALIN EC (40% ACTIVE) POTENCY EXPERIMENT: EMERGENCE OF WEEDS VS RATE MALLEE SOIL - IMMEDIATE AND DELAYED INCORPORATION

| | | | % Emergence |
|---|---|---|---|
| Rate 1/ha | $Log_{10}$ (rate + 1) | Imm. Inc. | Del. Inc. |
| 0 | 0 | 95 | 85 |
| 0.1 | 0.05 | 97 | 87 |
| 0.2 | 0.09 | 73 | 77 |
| 0.3 | 0.12 | 34 | 89 |
| 0.4 | 0.15 | 20 | 84 |
| 0.6 | 0.2 | 5 | 60 |
| 0.8 | 0.26 | 2 | 32 |
| 1 | 0.3 | 1 | 18 |
| 1.5 | 0.4 | 0 | 3 |

TABLE 10 (b)

TRIFLURALIN FORMULATION H POTENCY EXPERIMENT: EMERGENCE OF WEEDS VS RATE MALLEE SOIL - IMMEDIATE AND DELAYED INCORPORATION

| | | | % Emergence |
|---|---|---|---|
| Rate 1/ha | $Log_{10}$ (rate + 1) | Imm. Inc. | Del. Inc. |
| 0 | 0 | 95 | 80 |
| 0.1 | 0.05 | 85 | 85 |
| 0.2 | 0.09 | 55 | 92 |
| 0.3 | 0.12 | 10 | 86 |
| 0.4 | 0.15 | 6 | 81 |
| 0.6 | 0.2 | 2 | 40 |
| 0.8 | 0.26 | 1 | 10 |
| 1 | 0.3 | 0 | 2 |
| 1.5 | 0.4 | 0 | 3 |

EXAMPLE 12

An emulsion suitable for use as a pre-emergent herbicide was prepared using the following components according to the procedure below.

| Component | Part |
|---|---|
| Oil Phase | |
| Trifluralin | 26 |
| Chinese rosin | 19.5 |
| Solvesso 150 | 19.5 |
| Dobenz CA | 0.5 |
| Water phase | |
| Water | 28.5 |
| Polyetheylenglycol (MW300) | 4 |
| Nonionic surfactant* | 2 |

*see Example I

METHOD

In a 1 liter container were added 240 g of trifluralin and 180 g of Chinese rosin, and heated to 105° C. with stirring until homogeneous. Weight loss was 1.5 g (0.36%). 180 g of Solvesso 150 was added and the mixture was stirred, the temperature thereby dropping to 75° C. The mixture was further stirred until the temperature reached 58° C. Weight loss was 0.5 g which was replenished by Solvesso 150. The mixture was decanted into jars which were tightly sealed. The mixture remained liquid at −5° C.

In a 100 ml beaker was added 0.4 g of Dobenz CA and 52 g of the above-mentioned mixture (oil phase), and heated with stirring to 95° C.

The water phase was prepared by adding 1.6 g nonionic surfactant* 3.2 g of PEG 300 and 22.8 g of boiling water to a 100 ml beaker.

The beaker containing the water phase was agitated using the 16 mm disintegrating head on a Silverson homogenizer. The oil phase was gradually added, and care was taken to ensure that the surface of the liquid in the beaker was continuously homogenised by adjusting the height of the disintegrating head. When addition of the oil phase was complete, the emulsion was further homogenised for 30 minutes.

* see Example 1

EXAMPLE 13

METOLACHLOR FORMULATION 1

The emulsion in this example contained the herbicide metolachlor which is of the chloro acetanilide class.

| MATERIALS | |
|---|---|
| Metolachlor | 36 |
| Bitumen C170, PD tar free | 42 |
| Di-isodecyl phthalate | 24 |
| Xylene | 18 |
| Nonionic surfactant* | 6 |
| Dobenz CA | 4 |

The water phase consisted of 280 parts.
* see Example 1

METHOD

Metolachlor, bitumen, di-isodecyl phthalate and nonionic surfactant were mixed at 110° C. until homogeneous. Xylene and Dobenz CA were added and the weight loss replenished using xylene. The above oil phase was slowly added to water which was agitated using a Silverson homogenizer.

BIOASSAY PROTOCOL

This protocol was as for the volatile loss of active in Example 3 with the following modifications:

(i) The metolachlor was sprayed through a laboratory sprayer capable of simulating field conditions. Applications were at a pressure of 200 kpa, through nozzles giving a 100 degree flat fan in 64 1/ha water and at 6 kilometers per hour.

(ii) Formulations were applied at 0, 18, 36, 72, 144, 216, 288 and 432 g metolachlor/ha.

(iii) All treatments were incorporated immediately after spraying and punnets were then each sown to 25 seeds of annual rye grass (holium rigidum).

(iv) Treatments were assessed for emergence 10 days safter spraying and all seedlings with a height in excess of 20 mm were counted as having satisfactorily emerged.

RESULTS OF EXAMPLE 13

Figure 10:
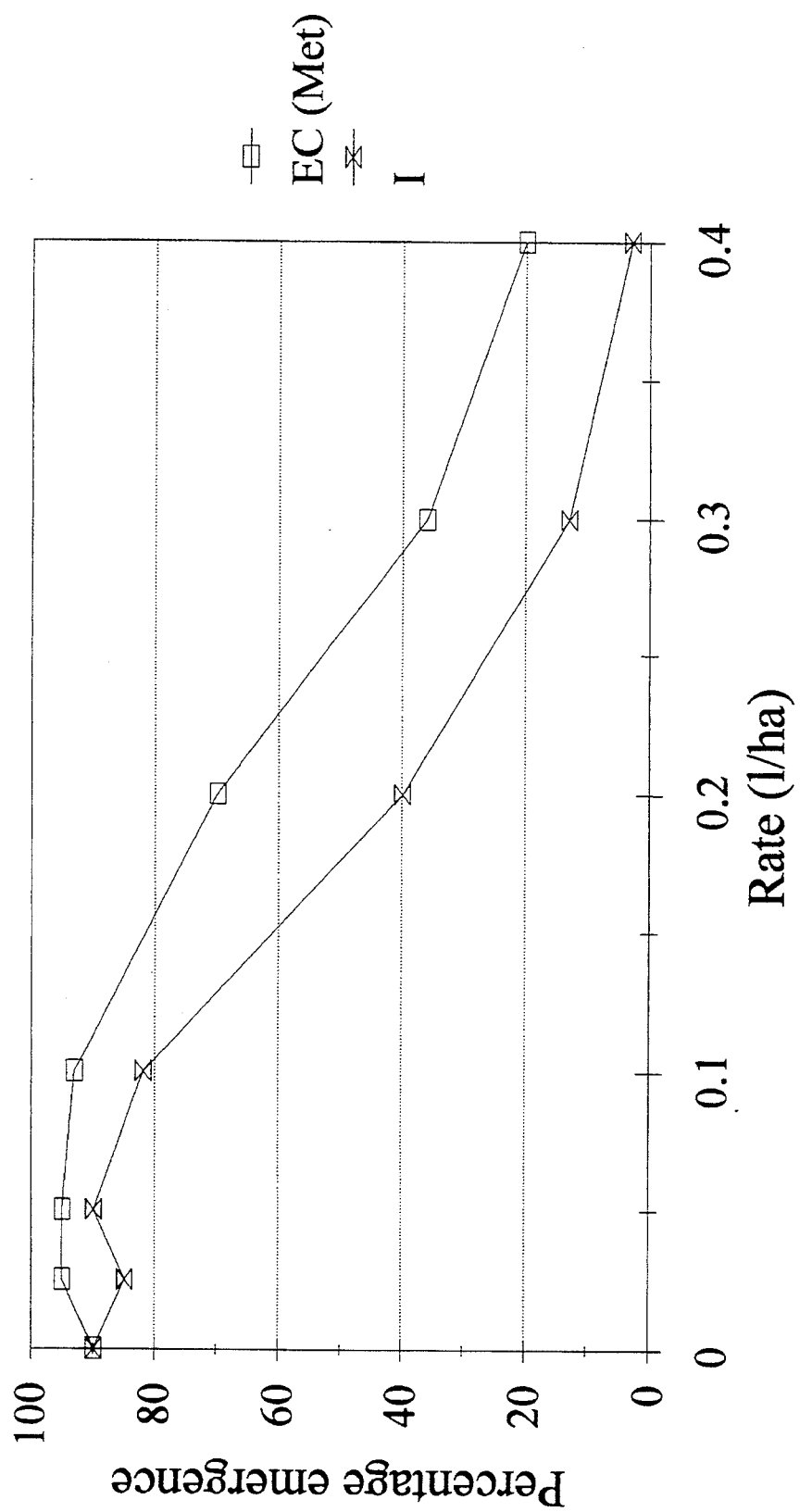

The results are tabulated in Table 11 and graphed in FIG. 10. FIG. 10 also shows control data for the performance of EC (Dual, 72% active supplied by Ciba-Geigy Australia) which should be compared with Formulation 1. It was concluded that Formulation 1 was significantly more potent than EC.

TABLE II

METOLACHLOR FORMULATION I
POTENCY EXPERIMENT - EMERGENCE OF
WEEDS VS RATE MALLEE SOIL.
IMMEDIATE INCORPORATION EC (72% ACTIVE)
AND METOLACHLOR FORMULATION I

| Rate (1/h) EC equivalent | $Log_{10}$ (rate + 1) | EC | % Emergence Metol. I |
|---|---|---|---|
| 0 | — | 90 | 90 |
| 0.03 | — | 95 | 85 |
| 0.06 | — | 95 | 93 |
| 0.11 | — | 93 | 84 |
| 0.2 | — | 70 | 41 |
| 0.3 | — | 37 | 14 |
| 0.4 | — | 20 | 4 |

Example 14

METOLACHLOR FORMULATION J

BENEFIT OF FORMULATION: Increased potency of metolachlor.

MATERIALS

| Metolachlor | 36 |
|---|---|
| Bitumen C170 PD tar free | 66 |
| Xylene | 18 |
| Nonionic surfactant* | 6 |
| Dobenz CA | 4 |

The water phase consisted of 280 parts,
* see Example 1

METHODS

As for Example 13.

BIOASSAY PROTOCOL

As for Example 13.

RESULTS OF EXAMPLE 14

Figure 11:
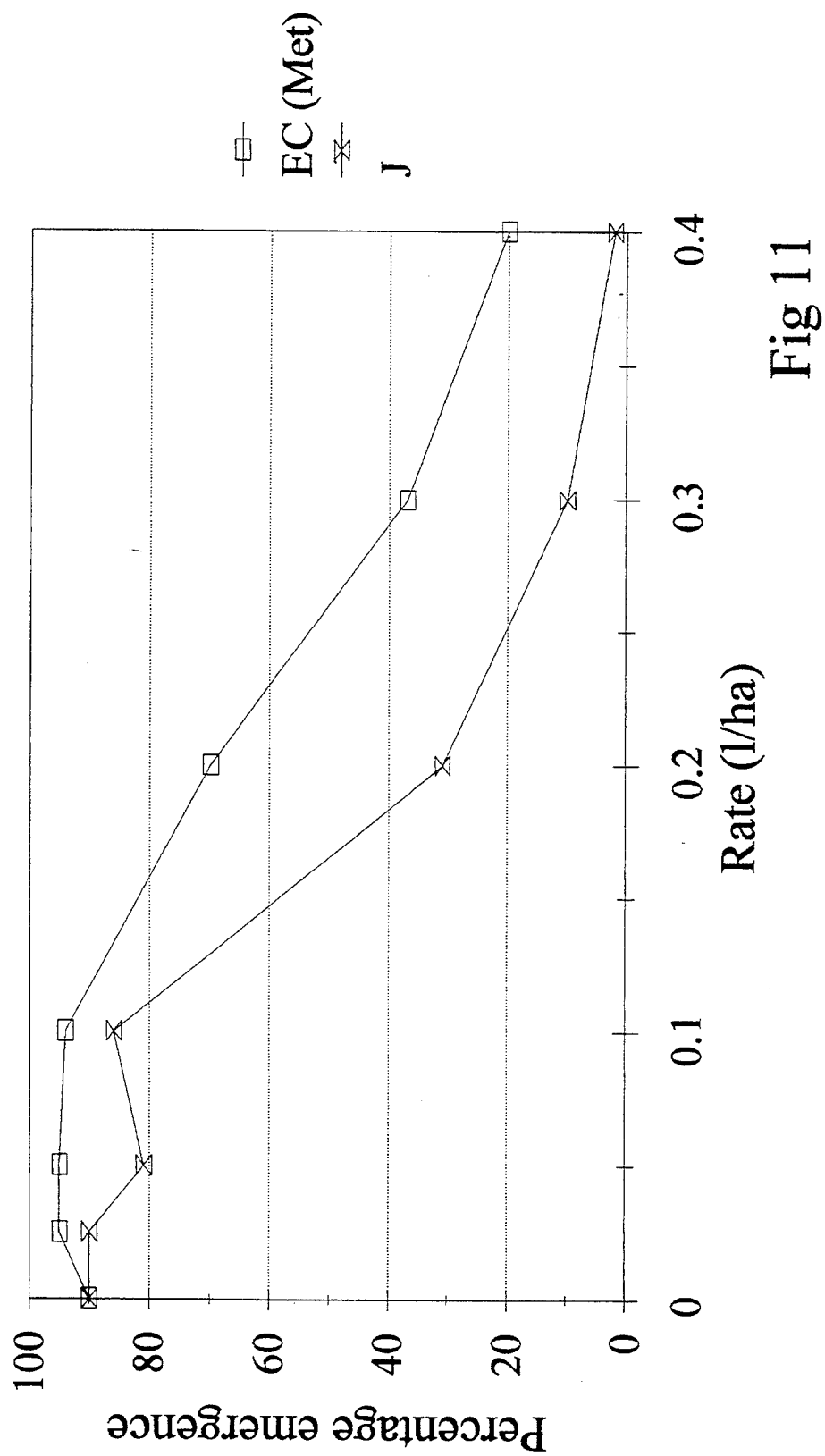

The results are tabulated in Table 12 and graphed in FIG. 11. FIG. 11 also shows control data for the performance of EC which should be compared with Formulation J. It was concluded that Formulation J was significantly more potent than EC.

TABLE 12

METOLACHLOR FORMULATION J
POTENCY EXPERIMENT - EMERGENCE OF
WEEDS VS RATE. MALLEE SOIL.
IMMEDIATE INCORPORATION. EC (72% ACTIVE)
AND METOLACHLOR FORMULATION J

| Rate (1/h) EC equivalent | $Log_{10}$ (rate + 1) | EC | % Emergence Metol. J |
|---|---|---|---|
| 0 | — | 90 | 90 |
| 0.03 | — | 95 | 90 |
| 0.06 | — | 95 | 81 |
| 0.11 | — | 93 | 88 |
| 0.2 | — | 70 | 31 |
| 0.3 | — | 37 | 10 |
| 0.4 | — | 20 | 3 |

EXAMPLE 15

CHLORPYRIFOS FORMULATION K

BENEFIT OF FORMULATION: Reduced volatile loss of chlorpyrifos.

MATERIALS

| | |
|---|---|
| Chlorpyrifos (technical, ex. Nufarm) | 6 |
| Rosin ester | 21 |
| Nonionic surfactant* | 1.1 |
| Dobenz CA | 1.9 |

The water phase consisted of 70 parts of water and 0.1 parts keltrol, a cellulosic thickener consisting of a high molecular weight xantham gum made by Kelco Division of Merc & Co USA.

* see Example 1

METHOD

Nonionic surfactant, rosin ester and chlorpyrifos were heated at 145° C. and stirred until homogeneous. Subsequently Dobenz CA was added and the mixture was again stirred. The emulsion was formed by adding oil phase (115° C.) to boiling water in the presence of high shear agitation supplied by a Silverson homogenizer. After addition of the oil phase was complete, the emulsion was cooled to 40° C. and Keltrol was added with rapid agitation for a further 2-3 minutes.

BIOASSAY PROTOCOL: Reduced volatile loss (a) GLASS SUBSTRATE

Glass petri dishes were treated with 1 ml of insecticide formulation (log series from $10^{-9}$ to $10^{-4}$ grams active ingredient/ml). Five replicates of each dose for each formulation were treated and left to dry overnight. On day 2, freshly emerged adult. Apanteles Subandinus (10 individuals) were added to each replicate plus 5 untreated controls. Mortality was assessed after 24 hours (day 3).

(b) LEAF BIOASSAY, GLASS-HOUSE

Potato plants (S. Tuberosum) were grown in pots in a glass-house (temperatures up to 35° C.) and each plant was sprayed by hand until runoff with formulations of chlorpyrifos ($10^{-7}$ grams active ingredient per ml). Leaves were picked on several days after spraying and bioassayed at 23° C. with Apanteles Subandinus. Disks (2 cm diameter) were cut from the leaves and placed in a glass petri dish (10 discs/petri dish) with A. Subandinus (10/ dish). 5 petri dishes were used for each formulation and the control. The mortality of A. Subandinus was assessed as for the above bioassay.

RESULTS OF EXAMPLE 15

The results are tabulated in Tables 13(a) and 13(b) for the glass substrate and leaf bioassay respectively, and control data is also shown for the performance of the EC (Lorsban, by Dow Elanco). The results are also graphed in FIGS. 12(a) and 12(b). On the glass substrate test (FIG. 12(a)) chlorpyrifos formulation K killed A. Subandinus at much lower dose than Lorsban. The estimated LD50 for Formulation K was two orders of magnitude lower than for Lorsban.

Figure 12B:
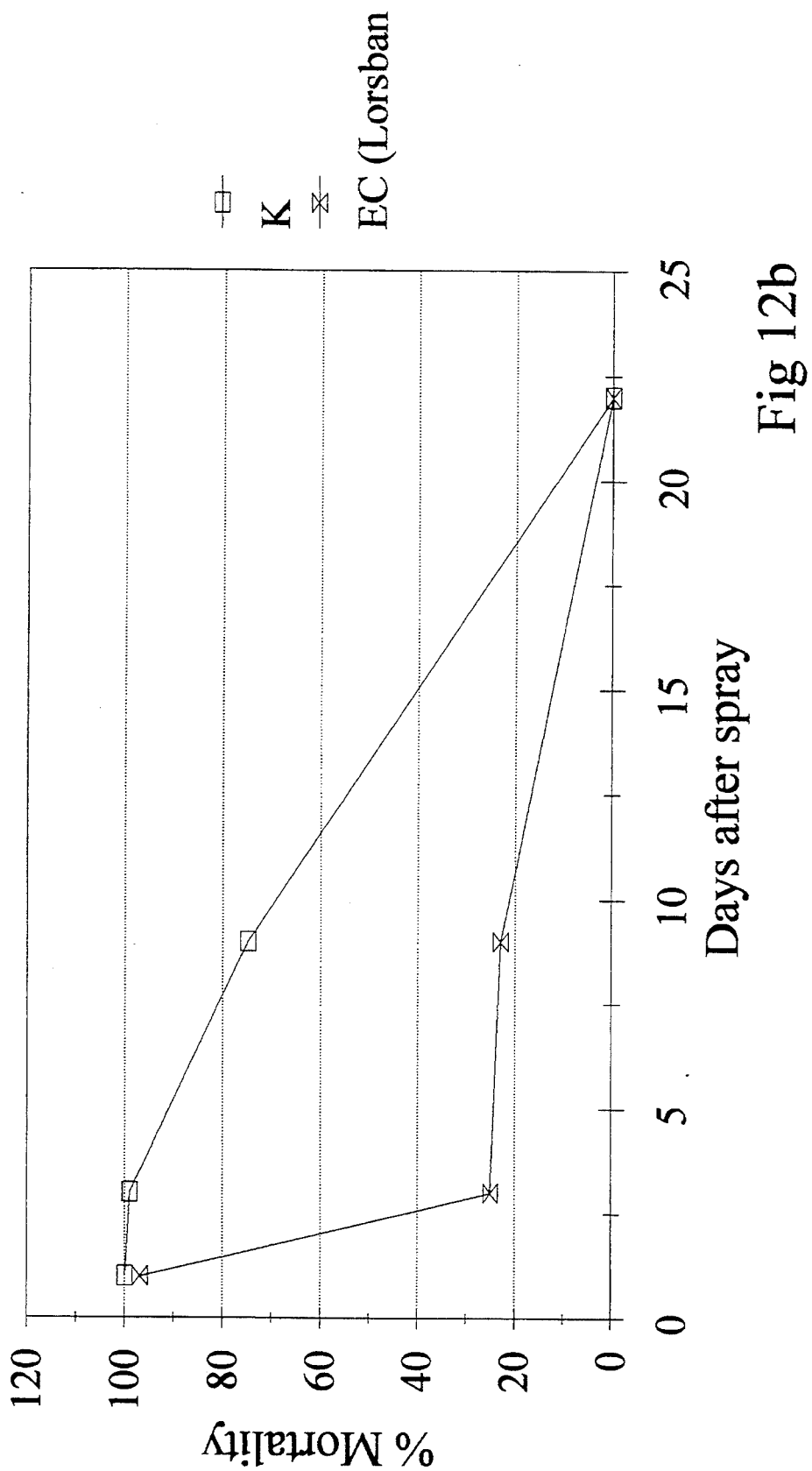

On the leaf substrate (glass-house) test (FIG. 12(b)), Lorsban killed high numbers of A. Subandinus for only one day while chlorpyrifos formulation K killed high numbers for over 7 days.

TABLE 13(a)

CHLORPYRIFOS FORMULATION K
VOLATILE LOSS EXPERIMENT:
Glass Substrate EC (Lorsban 50) and Formulation K

| Dosage | Percent Mortality | |
|---|---|---|
| (Micrograms chlorpyrifos per dish) | EC | Formulation K |
| 1,000 | 100 | 100 |
| 20 | 100 | 100 |
| 2 | 26 | 100 |
| 0.2 | 8 | 90 |
| 0.02 | 5 | 8 |

TABLE 13(b)

CHLORPYRIFOS FORMULATION K
VOLATILE LOSS EXPERIMENT:
Leaf Bioassay EC (Lorsban 50) and Formulation K

| | Percent Mortality | |
|---|---|---|
| Days After Application | EC | Formulation K |
| 1 | 100 | 100 |
| 3 | 25 | 100 |
| 9 | 22 | 75 |
| 22 | 0 | 0 |

EXAMPLE 16

CHLORPYRIFOS FORMULATION L

BENEFIT OF FORMULATION: Reduced volatile loss of chlorpyrifos

MATERIALS

| | |
|---|---|
| Chlorpyrifos | 48 |
| Rosin ester | 60 |
| Nonionic surfactant* | 6 |
| Dobenz CA | 6 |
| Water | 280 |
| Keltrol | 0.6 |

The method was as for Example 15.

* see Example 1

BIOASSAY PROTOCOL: Reduced volatile loss, glass substrate (as for E15)

RESULTS

The results were that the estimated LD 50 for Formulation L was 2 orders of magnitude lower than for Lorsban and data are shown in Table 14.

TABLE 14

CHLORPYRIFOS FORMULATION L
VOLATILE LOSS EXPERIMENT - GLASS SUBSTRATE

| Dosage | Percent Mortality | |
| --- | --- | --- |
| (micrograms chlorpyrifos per disk) | EC | Formulation L |
| 1,000 | 100 | 100 |
| 20 | 100 | 100 |
| 2 | 22 | 100 |
| 0.2 | 10 | 66 |

Since modifications within the spirit and scope of the invention may be readily effected by persons skilled in the art, it is to be understood that the invention is not limited to the particular embodiments described, by way of example, hereinabove.

We claim:

1. A controlled release composition comprising an aqueous dispersion of a water insoluble matrix as a disperse phase wherein said matrix contains at least one active ingredient having a melting point of less than about 140° C. selected from the group consisting of herbicides, insecticides, fungicides and nematicides, and wherein said matrix comprises a viscous oil selected from the group consisting of bitumen, abietic acid, ester derivatives of abietic acid, carboxylic acid containing materials, and carboxylic acid ester containing materials; characterized in that said active ingredient is soluble in said matrix.

2. A composition according to claim 1 wherein said active ingredient has a melting point less than 120° C.

3. A composition according to claim 1 wherein said active ingredient has a melting point less than 80° C.

4. A composition according to claim 1 wherein the active material is either a chloroacetanilide or dinitroaniline herbicide or an organophosphate insecticide.

5. A Composition according to claim 1, further comprising at least one surfactant selected from the group consisting of non-ionic surfactants, and anionic surfactants.

6. A composition according to claim 5, wherein a said anionic surfactant is a calcium salt of an alkyl benzene sulphonic acid, and a said non-ionic surfactant comprises a polyethylene oxide and polypropylene oxide copolymer or adduct thereof.

7. A composition according to claim 1 wherein the composition further comprises a non-volatile diluent having ester functionality.

8. A composition according to claim 1 or 7, wherein said composition further comprises a volatile solvent at a ratio of solid volatile solvent to active ingredient of about 0.5 to 1.5.

9. A composition according to claim 1, 7 or 8 wherein the active ingredient comprises at least 15% by weight of the composition and the disperse phase comprises at least 50% by weight of the composition.

10. A composition according to any one of claim 1 wherein the active ingredient is selected from the group consisting of trifluralin, chlorpyrifos and metolachlor.

11. A method of treating soil to retard the growth of vegetation thereon, comprising applying to the soil a controlled release composition according to any claim 9, wherein the active ingredient is a herbicide.

12. A method of rendering insects ineffective by using a controlled release composition according to claim 1, wherein the active ingredient is an insecticide.

13. A composition according to claim 1, wherein when said viscous oil is bitumen, said composition further comprises an anionic surfactant that is a calcium salt of an alkyl benzene sulphonic acid and a non-ionic surfactant that is a polyethylene oxide and polypropylene oxide copolymer or adduct thereof.

14. A composition according to claim 10 wherein when said active ingredient is trifluralin, said viscous oil is selected from the group consisting of rosin, Chinese rosin, and rosin ester.

* * * * *